US006902563B2

(12) United States Patent
Wilkens et al.

(10) Patent No.: US 6,902,563 B2
(45) Date of Patent: Jun. 7, 2005

(54) IRRADIATION DEVICE FOR THERAPEUTIC TREATMENT OF SKIN AND OTHER AILMENTS

(75) Inventors: Jan Hennrik Wilkens, Homburg (DE); Rolf Stirner, Berlin (DE)

(73) Assignees: OptoMed Optomedical Systems, Berlin (DE); Spectrometrix Optoelectronic Systems, Berlin (DE)

(*) Notice: Subject to any disclaimer, the term of this patent is extended or adjusted under 35 U.S.C. 154(b) by 0 days.

(21) Appl. No.: 10/094,430

(22) Filed: Mar. 8, 2002

(65) Prior Publication Data

US 2002/0161418 A1 Oct. 31, 2002

(30) Foreign Application Priority Data

Mar. 8, 2001 (DE) .................................... 201 09 899 U
May 10, 2001 (DE) ....................................... 101 23 926

(51) Int. Cl.⁷ ................................................ A61N 5/01
(52) U.S. Cl. .............................. 606/9; 128/898; 607/90
(58) Field of Search .......................... 606/9; 607/88–94

(56) References Cited

U.S. PATENT DOCUMENTS

| 3,521,111 A | 7/1970 | Tsuchihashi et al. |
| 3,540,789 A | 11/1970 | Przybilla |
| 4,167,669 A | 9/1979 | Panico |
| 5,184,044 A | 2/1993 | Thomas |
| 5,591,219 A | * 1/1997 | Dungan ..................... 607/88 |

(Continued)

FOREIGN PATENT DOCUMENTS

| EP | 0 565 331 A2 | 10/1993 |
| EP | 0 726 083 A2 | 8/1996 |
| EP | 0 565 331 B1 | 1/2001 |
| WO | WO 96/13851 | 5/1996 |
| WO | WO 00/02491 | 1/2000 |
| WO | WO 00/28575 | 5/2000 |
| WO | WO 00/53114 | 9/2000 |
| WO | WO 00/64537 | 11/2000 |

OTHER PUBLICATIONS

V. Sigurdsson et al., Phototherapy of Acne Vulagris with visible Light, Dermatologie 1997, 194; Bd. 3, 256–260.
McGinley et al., Facial follicular porphyrin fluorescence. Correlation age and density of propionibacterium acnes, Br. J. Dermatol vol. 102., Bd. 3, 437–441, 1980.
ICNIRP (IRPA) –International Commission on NonIonizing Radiation Protection Association, Guidelines on limits of exposure to ultraviolet radiation of wavelength between 180 nm and 400 nm, Health Physics 49, pp. 331–340, 1985.
Proposed change to the IRPA 1985 guidelines in limits of exposure to ultraviolet radiation, Health Physics 56, pp. 971–972, 1989.

Primary Examiner—Roy D Gibson
Assistant Examiner—Henry M Johnson, III
(74) Attorney, Agent, or Firm—Frank J. Bonini, Jr.; John F. A. Farley, III; Harding, Earley, Follmer & Frailey

(57) ABSTRACT

The invention relates to an irradiation device and method for the treatment of totally or partially cell-mediated inflammations of the skin, the connective tissue and the viscera, viral and other infectious diseases such as HIV and prionic infections, fungal infections of the skin and the mucous membranes, bacterial diseases of the skin and the mucous membranes as well hand eczema and anal eczema which comprises at least one irradiation device to irradiate a surface treatment area where the wavelength of the emitted radiation to a treatment area is longer than 400 nm and comprises at least one spectral band between 400–500 nm while the radiation device contains means for the generation of optical pulses towards a treatment area with a power density of the optical pulse peaks larger than 0.5 W/cm² and smaller than 100 kW/cm². The energy of one pulse relates to 0.05–10 J/cm².

26 Claims, 14 Drawing Sheets

U.S. PATENT DOCUMENTS

| | | |
|---|---|---|
| 5,798,612 A | 8/1998 | Dirks |
| 5,964,749 A | 10/1999 | Eckhouse et al. |
| 6,021,344 A | 2/2000 | Lui et al. |
| 6,183,500 B1 | 2/2001 | Kohler |
| 6,223,071 B1 * | 4/2001 | Lundahl et al. ............... 607/91 |
| 6,280,438 B1 * | 8/2001 | Eckhouse et al. ............. 607/88 |
| 6,494,900 B1 * | 12/2002 | Salansky et al. ............... 607/89 |
| 6,514,242 B1 * | 2/2003 | Vasily et al. .................. 607/88 |
| 2001/0023363 A1 * | 9/2001 | Harth et al. ................... 607/90 |

\* cited by examiner

IRRADIATION DEVICE FOR THERAPEUTIC TREATMENT OF SKIN AND OTHER AILMENTS

BACKGROUND OF THE INVENTION

1. Field of the Invention

This invention relates to an irradiation device for therapeutic purposes, especially for the acute or chronic treatment of totally or partially cell-mediated inflammations of the skin, connective tissue and internal organs, viral and other infectious diseases such as HIV or prion infections, fungal diseases of the skin and the mucous membranes, bacterial diseases of the skin and the mucous membranes as well as hand eczema or anal eczema.

2. Brief Description of the Related Art

Therapeutic irradiation arrangements have been known for a long time, especially in the field of phototherapy of skin diseases. According to the particular application the patient is irradiated with wavelengths between 315–1500 nm. Particularly the range of wavelengths between 315–340 nm (UV-A2) carries an increased risk of carcinogenesis; so that especially in the treatment of atopic eczema the UV-A1 therapy (340–400 nm) is used.

Photochemotherapy as a general term includes the general use of optic irradiation for the attainment of therapeutic effects. A subspecialty of photochemotherapy is the photodynamic therapy (PDT). The main fields of PDT application are cancer treatment and the treatment of totally and partially cell-mediated skin inflammations. A common trait of both PDT applications is the generation of reactive oxygen species. This is accomplished by the optical radiation which excites systemically or topically applied dye molecules which are converted into an excited state. Through interaction with existing oxygen molecules reactive oxygen species are generated which then damage or destroy the cell.

Cancer therapy with PDT, which aims at the destruction of tumor cells, divides into two fields of application: The main indication is the treatment of the viscera. The procedure includes the optical irradiation of a laser being transported to the tumor via an optic fiber, thus irradiating a small punctiform area. In addition, the patient receives photosensitizers.

This presents the problem of a decreased perfusion of tumor tissue and therefore a decrease in oxygen in that part, which also limits the generation of reactive oxygen species. Therefore it is known practice in the tumor treatment of the viscera with PDT to have the patient inhale oxygen in order to increase the oxygen content of the tumor tissue and so encourage the generation of reactive oxygen species. Because of the increased consumption of oxygen it is known to pulse the irradiation source so that in the pulse-off interval fresh oxygen is allowed to diffuse into the tissue.

The second field of tumor treatment with PDT is the treatment of superficial tumors such as especially melanoma, where no additional oxygen is given because of the naturally existing oxygen.

Other than tumors, wholly or partly cell-mediated skin inflammations usually cover large areas of skin, so that irradiation sources which can cover larger areas, for example 5 cm²–2 m² at a time, are the medium of choice here. Another difference to tumors is the increased blood flow in inflammations that is recognizable by an erythema in the inflamed area. Furthermore, there is no exogenous application of sensitizers, so that even if we assume a phototherapeutically induced involvement of singlet oxygen (for example, by using the photodynamic effect of endogenous porphyrins) we can conclude that even a considerable decrease of oxygen concentration has little or no important effect on the decrease of triplet efficiency in the skin. Besides this, the maximum concentration of endogenous photosensitizers is several orders of magnitude below the concentration which can be effected by systemic or topical application. The aforementioned good perfusion is the reason that a combined photo/oxygen therapy has not been tried yet in the treatment of cell-mediated diseases.

The PDT method that is chiefly used in the treatment of wholly or partly cell-mediated diseases is a high-dose UVA1-Therapy, using a wavelength range between 340–400 nm. This requires the employment of high doses of, for example, over 60 mW/cm² to get satisfactory therapeutic effects. In spite of that, 20–30% of the treated patients do not respond to a UVA1-Therapy.

It is known to treat acne, which is a skin disease caused by proliferation of bacteria in blocked follicles of areas of the skin that are rich in sebaceous glands together with keratosis, with blue light in the range of 400–440 nm without significant proportions of UVA, with limited success.

Here we refer to the article of V. Sigurdsson et al., Phototherapy of Acne Vulgaris with visible Light, Dermatologie 1997, 194; Iss.3, 256–260 which includes further literature references. This form of therapy started by using red fluorescence of acne follicle as part of the dermatological examination using Wood's Lamp. The source determined for the fluorescence was the storage of large quantities of porphyrins in the propionbacterium acne. McGinley et al., Facial follicular porphyrin fluorescence. Correlation with age and density of propionibacterium acnes, Br. J. Dermatol. 1980, Vol. 102, Iss. 3, 437–441). Since the principal absorption (Soret-band) of porphyrins is around 420 nm, it was obvious for Meffert et al. to treat acne follicles with blue light. The longest-wave absorption band of porphyrins is 630 nm, with a penetration depth of 4 mm, which is most favorable for photodynamic follicle treatment and is used for this purpose.

From WO 00/02491 such an irradiation device is known which comprises at least one narrowband spectrum in the range of 405–440 nm. As alternative or cumulative areas of the spectrum the wavelength intervals between 610–670 and 520–550 nm are given. For further improvement of treatment efficacy it is proposed to increase the oxygen concentration within the irradiated area by applying oxygen-enriched emulsions before or during the irradiation. The irradiation intensity for this is between 10–500 mW/cm².

From EP 0 565 331 B1 a device for the treatment of vascular diseases in an area of the skin is known, including a housing with an incoherent light source mounted in that housing and suitable for the emission of pulsed light for treatment, and an opening in the housing, defining a ray of light which is emitted onto the afflicted area of skin without passing through a cable of optical fibers, thus showing a wider irradiation area than devices with optical fibers, the device also including a low cutoff filter, thus cutting off the visible and UV parts of the spectrum while the incoherent light source emits a ray of light combining wavelengths between 300 and 1000 nm. The light source has an electrical connection to a pulse-forming-network in order to deliver a time pulse between 1 and 10 ms, the emitted ray of light producing an energy density between 30 and 100 J/cm², so that the emitted light may pass through a low cutoff filter and penetrate the skin as deeply as desired without burning of the skin, in order to heat a blood vessel under the skin in the skin treatment area and to cause blood coagulation in the blood vessel. The blood coagulation described there is to be avoided in the treatment of wholly or partially cell-mediated skin inflammations or acne, so that the described device is not suitable for PDT.

From U.S. Pat. No. 5,964,749 an irradiation device for the tightening of skin is known, including a source of irradiation emitting pulsed light in the range of 600–1200 nm, by which heat is coupled into the tissue below the threshold of necrosis, causing the collagen of the skin to shrink. The pulse energies here range mostly around 1 J/cm$^2$. The pulse irradiation peaks show a power of 100–1000 W/cm$^2$. The preferred total energy for one treatment is given as 100 J/cm$^2$.

From WO 00/53114 an irradiation arrangement for skin tightening is known, including an irradiation source emitting pulsed light in a wavelength interval of 500–850 nm, the pulse energy being less than 5 J/cm$^2$.

From WO 00/28575 a irradiation arrangement for therapeutic and cosmetic purposes is known for the treatment of primarily T-cell-mediated skin diseases, especially of atopic dermatitis, cutaneous T-cell-lymphoma, lichen ruber, alopecia areata, systemic Lupus erythematodes and psoriasis, the irradiation device comprising at least one source of optical irradiation, generating on the afflicted area an intensity of at least 2 mW/cm$^2$ in a wavelength interval of 400–440 nm, and less than 21% of that intensity in a wavelength interval of 300–400 nm. The irradiation device utilizes the astonishing efficiency of the radiation in the range of 400–440 nm, which offers an irradiation device for the treatment of primarily T-cell mediated skin diseases with which it would be possible to treat skin diseases like lichen ruber that have so far almost defied treatment, and, due to its drastically reduced carcinogenity over UVA, also offers the possibility for the treatment of children.

This patent also mentions the fact that for the mode of efficiency of blue light there are patient-specific threshold values for the intensity of irradiation. This statement is based on the specific content of melanin and/or antioxidants in each patient's skin, so that irradiation intensities of over 60 mW/cm$^2$ resp. over 100 mW/cm$^2$ are preferably applied.

From EP 0 726 083 A2 a therapeutic irradiation arrangement for the treatment of cancer cells in tissue is known, which features a diagnostic and a treatment mode. The source of radiation is a broadband flashlamp the spectrum of which is modified by filters according to the operation mode. In treatment mode the source emits light in the range of 600–1000 nm or 600–700 nm, the pulses showing an energy density between 0.1–20 J/cm$^2$. The intensity here is between 100–2000 mW/cm$^2$. The diagnostic mode utilizes the fluorescence of cancer cells in blue light. This fluorescence can be recorded and analyzed with a suitable optical arrangement. For this purpose, the tissue to be examined is irradiated with pulses of a spectral range between 350–500 nm with a peak at 400 nm. The pulse frequency lies between 0.02–2 Hz, with a pulse length between 0.1–1000 ms. The light is coupled into a quartz cylinder or an optic fiber with an energy density between 0.02–4 J/cm$^2$. The size of the examined area depends on the distance between quartz cylinder resp. optic fiber and skin surface. Due to the non-coherence of the radiation, only a fraction of the radiation energy can be coupled into the optic fiber. It is, however, possible to couple most of the energy into the quartz cylinder, but here the light rays are extremely expanded on leaving the cylinder. On an area of, for example, 0.5 cm$^2$ and an observation distance of 5 cm the energy density on the treatment area decreases by a factor of 500. These observation distances are, however, necessary in order to watch the fluorescence, which is illustratively described in U.S. Pat. No. 6,021,344. This causes a rather low energy density of 0.04–8 mJ/cm$^2$ on the skin, which is sufficient for diagnostic purposes.

SUMMARY OF THE INVENTION

This invention is based on the technical problem of providing an irradiation arrangement for the treatment of acute or chronic wholly or partially cell mediated inflammations of the skin and the viscera, the treatment of viral and other infectious diseases such as HIV or prion diseases, fungal infections of the skin and the mucous membranes, bacterial diseases of the skin and the mucous membranes as well as hand eczema or anal eczema.

For this purpose, the irradiation arrangement comprises at least one radiation source for the irradiation of an extensive area, the wavelength of the radiation emitted being higher than 400 nm and including at least one part in the wavelength range between 400–500 nm, the irradiation arrangement including means for the generation of optical pulses on the treated area, the radiation intensity of the optical pulse peaks being between >0.5 W/cm$^2$ and <100 kW/cm$^2$, the energy density of one emitted optical pulse being between 0.05–10 J/cm$^2$. The data for radiation intensity and energy density relate to the area to be irradiated, when the irradiation device may also be brought into direct contact with the skin surface. The term "extensive" here relates to an area bigger than 0.1 cm$^2$. Over 400 nm means that less than 7% of the overall optical output are emitted in the UV range, whereas at least 30% of the optical output are emitted in the range of 400–500 nm. The percentage of UVB and UVC is negligibly small—under 0.1% of the overall emission—so that the remaining part of UV-emission is UVA1 and UVA2, the ratio being 1:10, which means the main part of the remaining UV-emission lies in the range of UVA1, between 340–400 nm. Another preferred embodiment has a remaining UV percentage of less than 3.5–5% of the overall optical emission and more than 40% of the overall optical emission at the range of 400–500 nm.

The present invention utilizes the discovery that during pulsed irradiation—other than described in the scientific literature—the generation of singlet oxygen during peak power time is higher than during cw-irradiation by several orders of magnitude. Another advantage of high peak powers is the fact that the deeper layers of the skin also receive sufficient irradiation intensity, seeing that usually only a fraction of cw-radiation reaches those deeper layers due to the low penetration depth of blue light. In addition, pulsed radiation energy has a stronger photobiological effect. If we assume an equal cumulated radiation dose of cw-radiation and pulse radiation, and also assume an intensity of 70 mW/cm$^2$ for the cw-radiation, we would see that only 10 mW/cm$^2$ would remain for photobiological effects, since 60 mW/cm$^2$ of the radiation input would be neutralized by dermal antioxidants as a constant off-set. It is obvious that this decrease in photobiological efficiency by constant off-set can be effectively reduced by using pulsed radiation. Pulsed power peaks in the kW power range are only marginally affected by this dermal antioxidant effect. The average energy supply is so chosen as to avoid necrosis of the cells but merely to induce apoptosis. Likewise, the treatment stays below the ablation threshold aimed at in EP 0 565 331 B1. Tissue ablation occurs when energy higher than 2500

J/cm² is deposited in the tissue within a period of time that does not allow heat exchange between adjacent layers. Due to the time modulation by pulse generation, where the irradiation time is below the relaxation period of the uppermost layer of the skin, in the outer layer of the skin hyperthermia is achieved which can easily be removed. Light in the range of 400–500 nm loses 50% of its energy after 200 μm. The estimated thermal relaxation period for a structure with a diameter of 200 pm is approx. 20 ms, meaning that, assuming a retention period of the light of <20 ms, only the outer layers of the skin are heated without any energy deposition in the deeper layers.

Besides the fields of application already described the irradiation arrangement can also be used for the disinfection of burn wounds or for the treatment of venous ulcers in the lower leg. Up to now, these have been treated with UV-light, which often leads to temporary improvement, but leads also frequently to complications in wound-healing in the long run. These short-lived effects are assumed to have their cause in the germicidal effect of UV-light, whereas the complications originate from irreparable cell damage. A UV-free, time modulated irradiation with optical pulses, preferably in the spectral range of 400–500 nm, more preferably in the range of 430–490 nm, will initially cause an oxidative damage in the cells, which can easily be repaired by eukaryotes because of their FPG-endonucleotidases. Prokaryotes such as staphylococci or streptococci, which do not have those enzymes, are much more sensitive to this kind of damage and can therefore be killed selectively.

Likewise, the irradiation arrangement can be used for the treatment of acne and acne scars. Here, among other mechanisms, collagenases are activated to cause a flattening of the scar. The same effects can be observed in the treatment of scleroderma, where the application of the irradiation arrangement can bring about an effective reduction of the collagen plaques. Furthermore, there was a marked effect on the circulating lymphocytes of patients with scleroderma by the use of pulse radiation. There was a particular decrease of killer lymphocytes of 75% after 5 irradiations. The number of circulating lymphocytes decreased by about 25%. These findings can be explained by the fact that activated lymphocytes become sensitive to the employed radiation through changes of their internal chromophores. The pulses can be generated either by a pulsed radiation source or by a relative motion of the radiation source over the area to be treated.

Preferably, the effective pulse lengths are between 1 μs and 500 ms. This relatively broad range stems from the different preferred effective pulse lengths for pulsed radiation sources and for relative motion in the form of a scanning device. The scanner, however, is preferably used for the treatment of skin diseases covering larger areas.

The preferred effective pulse lengths for flashlamps are between 1 μs and 50 ms, more preferably between 10 μs and 10 ms and most preferred between 100–600 μs, with the pulse on/off periods being asymmetric.

In the scanner embodiment the preferred effective pulse lengths are between 1 ms and 500 ms, more preferably between 20–100 ms. Effective pulse length means the period of time between the achievement of 50% of maximum performance and the drop to 50% of maximum performance. The off-period between pulses are longer than the effective pulse length in order to allow the diffusion of depleted oxygen. The ratio of pulse on/off periods is preferably between 3–3000 for the scanner and 100–100,000 for the flashlamp.

Another effect is the thermal cooling of the irradiated area during the pulse-off period, so that necrosis does not occur.

In another preferred embodiment the pulse frequency for the radiation source is between 0.01–100 Hz, more preferably between 0.05–50 Hz and further preferably between 0.3–3 Hz, using shorter effective pulse lengths and lower pulse energies with higher frequencies.

In order to improve the diffusion of oxygen and the thermal cooling, there is a longer pulse-off interval between a few seconds to a few minutes after a series of preferably, for example, 100 pulses, before generating a new pulse series. due to the extremely long diffusion times of oxygen there may also be applications where just one single pulse is administered before a longer pulse-off interval. These pauses can vary in length from one to several hours. Particularly for the treatment of chronic diseases the irradiation arrangement can be assigned to the patient as, for example, a belt, an irradiation blanket or an irradiation bed so as to give, for example, one pulse per hour. These long pauses make thermal problems or the diffusion of oxygen in tissues negligible.

Just as the effective pulse lengths are dependent on the use of either a pulsed radiation source or a source with relative motion, the preferred irradiation intensities resp. peak power densities per pulse are also different.

In embodiments with a pulsed radiation source the irradiation intensity per pulse is between 1 W/cm²–100 kW/cm², preferably between 50 W/cm²–50 kW/cm², more preferably between 500 W/cm²–10 kW/cm² and most preferably between 1 kW/cm²–5 kW/cm². The energy density per pulse is between 50 mJ/cm²–10 J/cm², preferably between 100 mJ/cm²–1 J/cm² and most preferably between 300–1000 mJ/cm². In embodiments with a scanner, where the radiation source may additionally also be pulsed, irradiation intensities per pulse are between 500 mW/cm²–500 W/cm², preferably between 1–300 W/cm² and most preferably between 50–200 W/cm². The energy density per pulse is between 50 mJ/cm²–10 J/cm² here, preferably between 100–1000 mJ/cm² and most preferably between 150–500 mJ/cm².

The higher energy densities between 1–10 J/cm² are preferably used for the treatment of very serious diseases, thus presenting the problem of sufficient cooling of the treated area.

The average cw-irradiation intensity of an optical pulse is preferably between 1 mW/cm² and 10 W/cm², more preferably between 5–500 mW/cm² and most preferably between 10–200 mW/cm². Average cw-irradiation intensity means the value of one pulse that would be continued with even intensity through one full period.

In another preferred embodiment the irradiation source is a Xe-flashlamp combined with an arrangement for the suppression and/or transformation of undesired parts of the spectrum into desired parts of the spectrum. These standard Xe-flashlamps are inexpensive and emit light of sufficient intensity in the desired part of the spectrum at wavelengths between 400–500 nm. Here we refer, for example, to U.S. Pat. No. 4,167,669 or EP 0 565 331, although the pulse energies described there are too high for the present invention, as in these inventions the ablation threshold is deliberately overstepped. Xe-flashlamps can, depending on their power density in the discharge channel, more or less be compared to a black body as to their spectrum, their typical emission being between 200–2000 nm. The undesired parts of the spectrum can be cut off by known standard filters. The desired blue part of the spectrum can be increased in a preferred embodiment by filling the Xe-flashlamp with gallium, indium and/or their resp. halides. Furthermore, the Xe-flashlamp can also be doped with mercury, mercury iodide or amalgam in order to increase the efficiency in the blue part of the spectrum. For pure Xe-flashlamps, the yield rates were best with electrodes of approx. 40 mm length and a diameter of 3.2 mm, the supply voltage being approx. 600 W. Alternatively, deuterium flashlamps are also applicable.

Another possible irradiation source is an overload-pulsed mercury iodide-gallium lamp. Overload is defined here as the maximum discharge energy being 3–1000 times the nominal lamp current, the pulse discharge energy being preferably between 15–1500 A/cm$^2$ cross-sectional area of the discharge vessel. A description of same standard metal-vapor mercury halide lamps can be found, for example, in U.S. Pat. Nos. 3,521,111; 3,540,789 and WO 96/13851.

U.S. Pat. No. 5,184,044 shows that with regard to the lamp geometry, the lamp performance of 20 W and the voltage drop of 55 V a lamp current of 8 A/cm$^2$ cross-sectional area of the discharge vessel corresponds to a maximally recommendable lamp load, since there is already an inversion of the indium spectrum. A further increase of current density would amplify the inversion up to total deletion.

Up to now, those have not been overload-operated, since even moderate overload operation can cause marked weakening or complete loss of spectral emission. Examples include the mercury emission at 254 nm, the sodium emission at 488 nm and the indium emission at 450 nm. Here we refer to U.S. Pat. No. 5,184,044 as an example. Furthermore, the discharge becomes inefficient with a higher load and an overload operation is economically not advisable.

Unexpectedly, it was discovered that gallium iodide-doped mercury medium-resp. high pressure lamps do show neither broadening nor an inversion of the gallium emission at 403 and 417, even if the overload is 100–1000 times above normal operating conditions. A gallium iodide-doped mercury discharge lamp run under normal conditions with a discharge current of 1.5 A/cm$^2$ cross-sectional area of the discharge vessel could be run in pulse operation mode with 1000 A/cm$^2$ cross-sectional area of the discharge vessel without reduction or inversion of the gallium emission lines. A possible explanation relates to the fact that metallic gallium has a boiling point of 2200° C. so that the gallium vapor pressure can be neglected even under pulse operation of the lamp. However, there is a disintegration of mercury iodide into mercury and iodine. During the plasma discharge, iodine forms an instable compound with gallium, gallium tri-iodide. GaI3 shows a marked increase of vapor pressure even at rather low temperatures. The absent inversion of the gallium emission could be explained by the fact that GaI3 is only stable up to a certain pressure and there is a rapid disintegration into gallium and iodine if the pressure is increased any further. Therefore a relatively stable gallium vapor pressure can be maintained even if there is rapid temperature increase during pulse operation. After the disintegration of the compound, GaI3 there is a condensation of metallic gallium which does not take part in the discharge and possible self-absorption of the gallium emission. This unexpectedly discovered effect could therefore be related to a paradox constant vapor pressure covering a temperature range between 200 and almost 2200° C. Mercury iodide disintegrates early into mercury and iodine, so that there is always iodine available to form a compound with the gallium. Mercury pressure therefore may increase rapidly with the energy load, thus providing excitational energy for the gallium emission. Due to the relatively stable gallium vapor pressure, most of this energy is emitted as gallium spectrum lines at 403 and 417 nm.

During overload operation, a temporary overheating occurs, particularly of the tungsten electrodes, which can emit considerably more heat at a rise of temperature, according to Planck's law. Therefore, a modulated lamp may be operated with an increased base load, since it is due to the temperature rise that the emission of input energy is considerably more efficient than in a normal-operated lamp. It so has turned out that a 1 kW-lamp can be operated with a steady load of 2–20 kW. Spectral measurements have shown the following: When a 1000 W mercury iodide gallium-doped lamp is cw-operated, approx. 400 mW/cm$^2$ in the spectral range of 400–440 nm reach the skin. This irradiation intensity can be decreased in simmer mode to an average irradiation intensity of 2–4 mW/cm$^2$, while the irradiation intensity during pulse load is temporarily increased by up to four to five orders of magnitude, so that irradiation intensities between 2 and 400 W/cm$^2$ reach the skin. The preferred ratio of pulse lengths lies between 3 and 300. This simple pulsed light source is also suitable for other technical applications such as, for example, dental curing, typographic applications, sealing of surfaces, pipe repair with light-cured tubing, plastic curing in the DVD production sector as well as the acceleration of other photochemical reactions that can be influenced by radical mechanisms of photoabsorption in the UV-blue range of the spectrum.

The ratio of gallium, resp. gallium additive and mercury should preferably be 1:10 to 1:100. In the performance range of 400 W the preferred ratio of components is 1–5 mg gallium iodide to 44 mg mercury.

Another typical lamp consists of a cylindrical quartz tube with diameter 13.5 mm and a discharge vessel with a volume of 20 cm3. The distance between the electrodes is 14 cm. This lamp is filled with 20 mg Hg, 3 mg mercury iodide, 1 mg gallium and argon with a pressure of 3.57 mm Hg.

The UV parts of the spectrum can also be transformed into the desired parts of the spectrum. For this, various kinds of foil have proven useful, the materials being silicone elastomers or fluorpolymers, particularly PTFE (Teflon), doped with anorganic phosphors. The silicone elastomers are preferably produced by additive polymerization, so that no volatile components such as water will come into contact with the anorganic phosphors The silicone elastomer is preferably produced by a composition of hydroxylpolydiorganosiloxane with an organohydrogensiloxane, the phosphors being added to the mixture and a chemical reaction being triggered by a platin catalysator at room temperature. The fluorescent foil has a preferred thickness of 10–800 μm, the density of the phosphor particles being preferably between 1–20 mg/cm$^2$, the grain size being 5–15 μm. The UVC-transparent carrier can also consist of silicone rubber, which can be cured without heat or pressure. Due to the considerable heat input, it has proven advantageous to cool the foil, thus extending its life span by several orders of magnitude. Depending on the heat input, the foil can be cooled by air or a water bath with the foil inside.

In another preferred embodiment a pulsed radiation source is operated in simmer mode, thus allowing to increase the pulse slope.

Alternatively, pulses of emitted radiation can be generated by an arrangement giving relative motion to the area to be irradiated. The simplest kind of arrangement would be an X- or X-Y-scan table, by which the patient can be moved back and forth under a cw-operable irradiation source. As an irradiation source for cw operation, basically radiation sources emitting in the blue range of the spectrum such as blue-emitting LEDs or equivalent gas discharge lamps, containing preferably gallium, indium or their respective halides come into consideration. The scan velocity here must be also be adapted in order to avoid the ablation threshold. Therefore, a focal line of a few mm thickness is generated that is moved length- or crosswise across the area to be treated with a velocity of 1–100 cm/s.

It is also possible to combine the scan movement with a pulsed radiation source, in order to further decrease the achievable pulse lengths for an assumed treatment area, which is also advantageous in view of thermal relaxation.

Particularly in the upper performance range the embodiment contains a cooling unit in order to avoid necrosis of the irradiated cells. Therefore, the cell temperature must be kept below 60° C. Type and size of the cooling unit here depend on the kind of energy administered and the intervals of administration. When using high energies, air cooling can be replaced by contact cooling, for example, by a cooled sapphire or a coolant that is sprayed directly on the skin. Another possibility for contact cooling is the use of cooled liquids, for example, water, oils or alcohol, which extract heat from the tissue through a latex or silicone membrane. The coolants ought to be optically transparent with lowest possible heat transition resistance. The more the skin can be cooled without causing damage, the higher energy input is possible without causing necrosis of the cells. Here, another advantage of pulsed radiation emerges. The gradients of heat input by optical pulses and cold input by cooling in the tissue vary from each other. The gradient of cold input is usually more shallow, so that there might be freezing damage due to crystallization. Through the pulses, however, there is a shock heating in the range of 100 $\mu$s, so that ice crystallization is disturbed, in spite of sub-freezing temperatures. Preferably, cooling and heat input are synchronized, for example, cooling is increased during the pulse. This regulation can be effected with the aid of a peltier element, the coolant temperature thus being lowered during the pulse from, for example, 4° C. to −(40–80)° C.

The efficiency of the irradiation arrangement can be increased by a raise of the oxygen concentration. Besides the measures described in WO 00/02491, this can be done by inspiratory oxygen supply via an oxygen mask. The advantage of inspiratory oxygen supply is the amplified supply of deeper tissue areas with oxygen by circulation, whereas we have to consider a certain gradient between the skin surface and the cells when using topical oxygen supply.

The average penetration depth of light depends very much on its wavelength, penetration depth increasing along with the wavelength. Therefore, a preferred embodiment also includes emission in the area of 520–550 nm and/or 610–670 nm, which can easily be achieved by adding the appropriate phosphors to the fluorescent material. Here, the proportion of red, resp. yellow for the irradiation of cells in the deeper layers is increased at the expense of the blue component. The blue component, however, is also important in the treatment of subsurface inflammations because of its germicidal properties, killing superficial bacteria that will colonize the skin in the aftermath of an inflammation and there again produce pro-inflammatory super-antigens.

In order to increase the output and concentrate it towards the area to be treated, the source of radiation preferably includes a reflector. This reflector can be designed as a paraboloid or as an ellipsoid. A paraboloid reflector would be used preferably for the temporal modulation of the emitted radiation by pulsing, whereas the ellipsoid reflector is used preferably for scan operation.

The preferred beam diameter of emitted radiation is wider than 4 mm, more preferably wider than 10 mm and most preferably wider than 40 mm. Here the fact is utilized that the penetration depth of light depends on the size of the irradiated area. Particularly a nearly punctiform irradiation has a very low penetration depth. Irradiation of larger areas causes an additive overlay of adjacent scattered photons in spite of light scattering in the upper layers. The consequence of this is a larger penetration depth compared to punctiform input at the same power density. Nonetheless, the beam diameter should not be too large and not exceed 200 mm, preferably 100 and most preferably 60 mm.

The previous consideration is based on the following:

By increasing the irradiated area, the energy density at the surface decreases so that the duration of the widened irradiation area may be longer. This accomplishes that a larger number of absorbing chromophores can be photochemically excited over a longer time interval than would be possible during a short pulse. The absence of radiation peaks within the radiation area impede the local bleaching resp. the local shortage of oxygen. Furthermore, there is a local maximum in the central area of the irradiation field since the scattering of all rays add and increase the radiation in the central area. Depending on the tissue parameters an the spectrum, the optimal irradiation area has a diameter of more than 4 mm and less than 60 mm since by using large diameters the scattering of the marginal rays does not increase the intensity in the central area. By choosing an optimal beam diameter, a higher intensity in the central irradiation area resp. a higher penetration depth can be achieved. A further widening of the irradiation area leads to a decrease in power density proportional to the increase of the area so that no light reaches the deeper tissue layers. Furthermore, the re-irradiation period of ever larger tissue areas shortens so that heat extraction resp. become more difficult.

The invention is described using embodiment illustrations.

BRIEF DESCRIPTION OF THE DRAWING FIGURES

FIG. 1 A cross-section of the irradiation device with a pulsed light source

FIG. 2 A spectrum of the radiation source with a luminescent foil

FIG. 3 A schematic view of the irradiation device with small angle rotation of the light source FIG. 4 A schematic view of the irradiation device with a one-dimensional scan movement FIG. 5 A schematic view of the irradiation device with a two-dimensional scan movement FIGS. 6a–c Different views of the penetration depth over an irradiated area FIG. 7 Illustration of the penetration depth as a function of the wavelength FIGS. 8a–c Different pulse modulation regimens FIG. 9 The effect of cw-operation and pulsed operation on the relative radiation intensity of a gallium iodide-doped mercury discharge lamp FIG. 10 Spectral energy density of a gallium iodide-doped mercury lamp at different power loads FIG. 11 Relative irradiance of a sodium vapor pressure lamp in cw- and pulse overload operation FIG. 12 Schematic circuit design for pulse operation of a gallium iodide-doped mercury lamp with two phases of a three phase current FIG. 13 Alternative circuit design with capacitor bank.

DETAILED DESCRIPTION OF THE PREFERRED EMBODIMENTS

The irradiation device 1 comprises a broadband irradiation source 2 which is preferably a xenon flashlamp. The irradiation source 2 is mounted in the focus of a parabolic reflector 3 which is open on the side averted from the focus. The exit area at the open end of the parabolic reflector 3 is preferably defined through an adjustable shutter. The adjustable shutter can adjust the area to be irradiated. The irradiation source 2 and the paraboloid reflector 3 are mounted in a housing 5. The housing 5 comprises a handpiece 6 by means of which the irradiation device 1 can be placed on the area to be treated 7. Between the radiation source 2 and the area to be treated 7 there is a luminescent foil 8 arranged which is doped with luminescent particles. The luminescent foil 8 can also be arranged in the proximity of the radiation source 2 or the shutter 4. Preferably, the luminescent foil 8 is arranged in a way that makes it easy to replace. This simplifies the necessary replacement due to aging but also the flexible use of luminescent foils with different luminescent particles. Furthermore, an externally mounted luminescent foil 8 can easily be disinfected. The electrical connectors and the pulse forming network for the generation of variable pulsewidths are not shown here for reasons of clarity.

FIG. 2 show a spectrum of the used xenon flashlamps with luminescent foil, while the discharge vessel is made of quartz glass. The luminescent foil is a silicone elastomer doped with inorganic phosphors which preferably emit within the blue region of the spectrum. the luminescent foil cuts off the UV part between 280–400 nm and transforms this part into the visible blue range between 400 and 450 nm. The illustration shows that the energy below 400 is less than 4.5% of the total optical power. Furthermore, this UV radiation is almost completely within the range of 340–400 nm and particularly in the range between 370 and 400 nm. Since this range of wavelength has a photobiological efficacy which orders of magnitude lower than that of the UVB or UVC range, the international limits for UV exposure are not exceeded. A definition of these values is given by the ICNIRP (IRPA)—International Commission on Non-Ionizing Radiation Protection Association "Guidelines on limits of exposure to ultraviolet radiation of wavelengths between 180 nm and 400 nm", Health Physics 49: 331–340, 1985 or "Proposed change to the IPRA 1985 guidelines on limits of exposure to ultraviolet radiation" Health Physics 56.971–972, 1989. the optical energy within the wavelengths between 400–500 nm is 43.6% and in the wavelength range of 400–450 nm 28.2% of the total optical power.

These measurings were done with a calibrated CDI spectrometer an 100 μm UV fiber.

The xenon flashlamp is operated with a frequency of 0.01 and 100 Hz while the effective pulse lengths are between 10 μs and 1 ms. The energy of the single pulses are preferably in the range of 0.3–0.8 J/cm².

FIG. 3 shows an alternative embodiment of the irradiation device 1 for the generation of light modulation. The radiation device 1 comprises a patient bed 9 on top of which the irradiation source 2 is mounted. The irradiation source 2 is enclosed by a paraboloid, ellipsoid or half cylinder reflector 3. The irradiation source 2 can be moved by a swivel mechanism not illustrated here by an angle ω out of the vertical position to the left and right. By this swiveling movement, different parts of the patients body can be irradiated so that there is a light modulation for each part of the body. The irradiation source may be pulsed or cw-operated. In an alternative embodiment the patient bed 9 can also swiveled in addition to the swiveling of the radiation source.

FIG. 4 shows an alternative embodiment of an irradiation device 1. The radiation source is designed in a line- or stripewise fashion and is movable above the patient bed 9 by the use of a mechanical fixation 11. This irradiation device 2 can be operated in pulse or cw mode. The scan movement in the arrow direction accomplishes also a light modulation for each part of the body. It is shown in FIG. 5 that the one-dimensional scan movement of FIG. 4 can be replaced be a two-dimensional scan movement.

Here, the radiation device 2 can additionally be moved oblique to the patient 10

The necessity of an area irradiation device is illustrated by FIGS. 6a–c. FIG. 6a shows a in cross-section which power densities can be found in which penetration level if the light power is emitted with a beam diameter of 20 mm. It can be seen that the lower density 15 mm under the surface is only 0.1 kW/cm². FIG. 6b shows the condition if the same available power is coupled into the tissue by a single fiber with a diameter of 1 mm. Under the assumption of a square radiation area the energy density of the surface has increased by factor 400. This leads to a very large gradient of the irradiation power with a peak density of 100 kW/cm² at the surface of the skin which leads to an ablation. If the same power density that is shown in FIG. 6a is coupled over a beam diameter of 1 mm, almost no optical power reaches the deeper layers of the tissue, which is shown in FIG. 6c. After a penetration depth of 5 mm, the power density has dropped to 0.1 kW/cm². FIGS. 6b and 6c illustrate that small diameters cannot reach large penetration depth without ablating the surface.

One single pulse has an effective length t1 between 100–2000 μs and is followed by a pulse-off period t2 between 10 ms–1000 s. The effective pulse length t1 is preferably between 100–500 μs and the pulse-off period between 100 ms–4 s. The preferred number of pulses lies between 10 and 10000, more preferred between 100 and 1000. The total pulse following period t3 results accordingly (t1+t2), multiplied with the number of pulses. This first pulse series is followed by a period t4 where no radiation is emitted so as to allow oxygen to re-diffuse into the tissue and allow the tissue to cool off, thus avoiding necrosis. The period t4 is preferably chosen between 1 min and 100 min, most preferring the longer periods. Subsequently, a new pulse series with a pulse following period t3 is generated. This period is again followed by a period t4. The total irradiation time t5 is chosen respectively to the seriousness of a disease between a few minutes to 2 hours. After an interval of several hours resp. 1–3 days the procedure is repeated. Systemic or topical dyes are not administered, so that the described procedure is not a PDT.

For a more detailed explanation we chose an example of a treatment of allergical contact eczema. The procedure includes two irradiation cycles per day, the periods t3 and t4 having a length of 5 minutes, the overall treatment time per day thus being 15 minutes. The pulse frequency is 0.5 Hz, so that during period t3 150 pulses are being applied. The effective pulse length t1 is 100 µs at a build-up time of approx. 10 µs. Thus, the pulse-off period t2 is approx. 2 s. The pulse peak is around 0.5 kW/cm$^2$, the energy density per pulse being between 0.4–0.5 J/cm$^2$ relatively to the wave slope. As a result we get an average cw-performance of 250 mW/cm$^2$ and an energy density of 120–150 J/cm$^2$ per day. Two treatment sessions per week result in a total energy density of 240–300 J/cm$^2$, the overall treatment period preferably being 4–8 weeks.

Moreover, the described irradiation therapy was performed with a frequency of 0.05 Hz, while maintaining the values for t1, t3 and t4 as well as for the radiation peaks. Due to the tenfold increase of t2 the administered energy density per treatment cycle and the average cw-performance decreased by factor 10 while producing similar treatment results. This may have its reason in a very slow oxygen diffusion, so that without additional oxygen administration next to no additional effect can be achieved by an increase of energy density.

Figure 1:
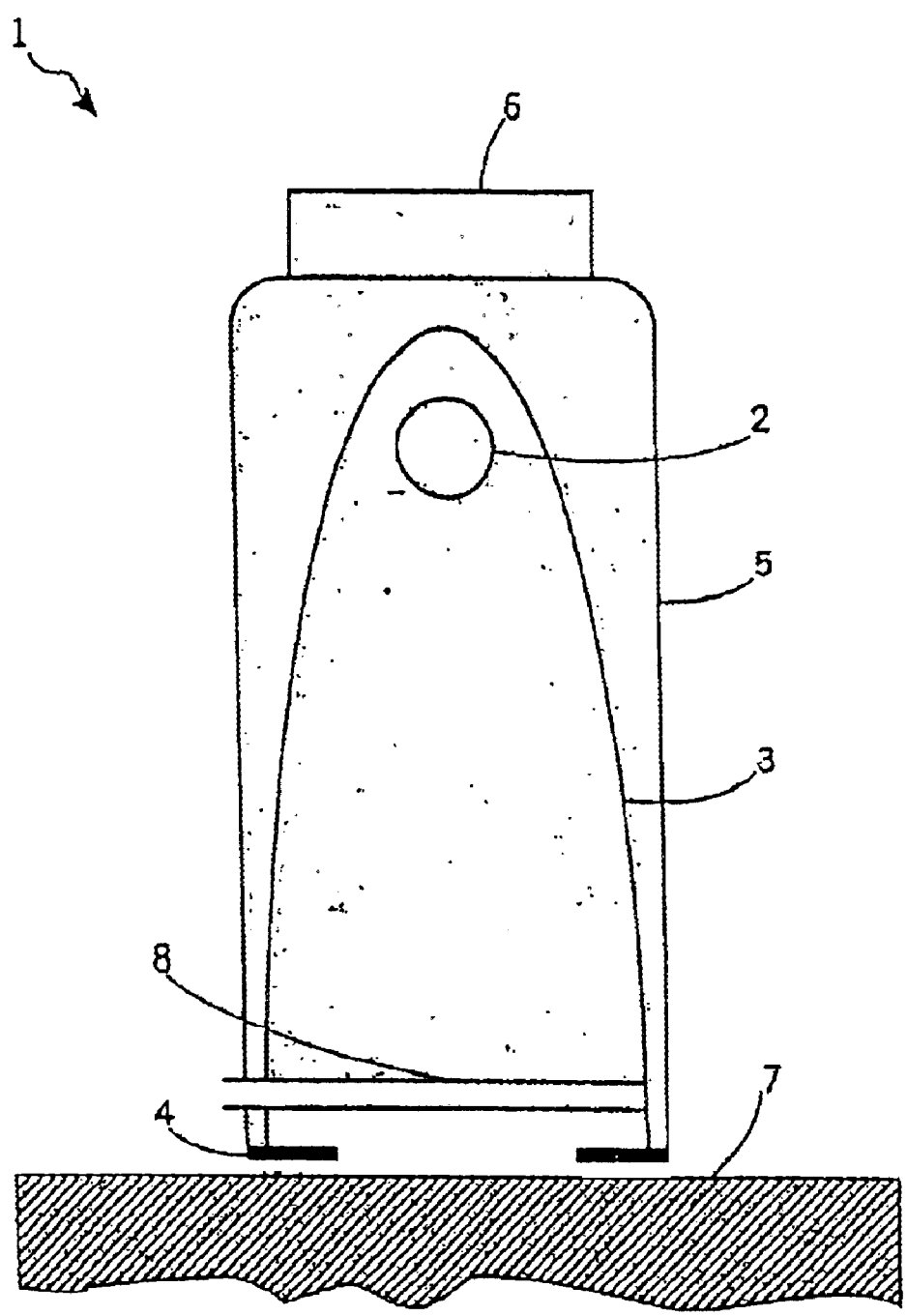
Figure 2:
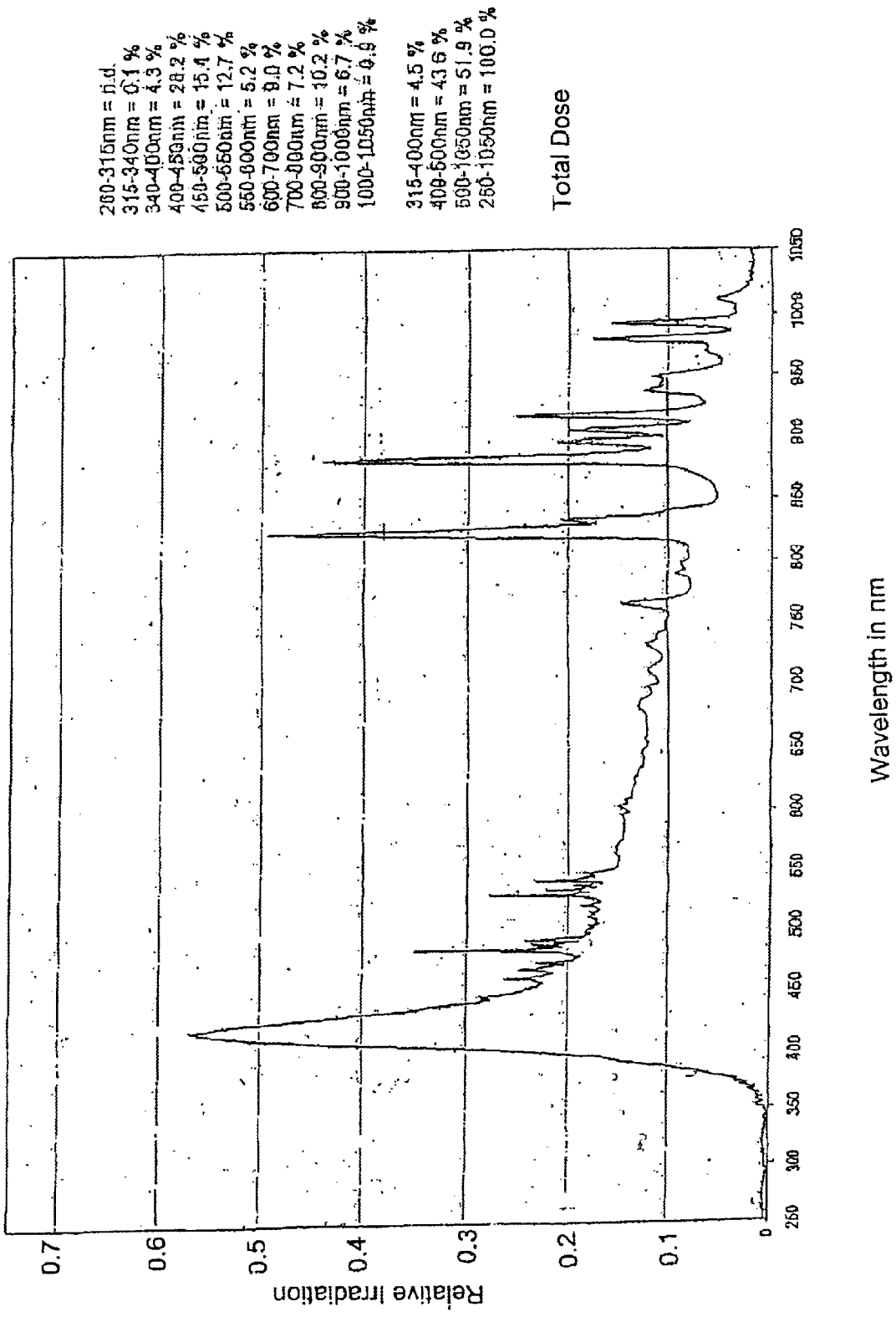
Figure 3:
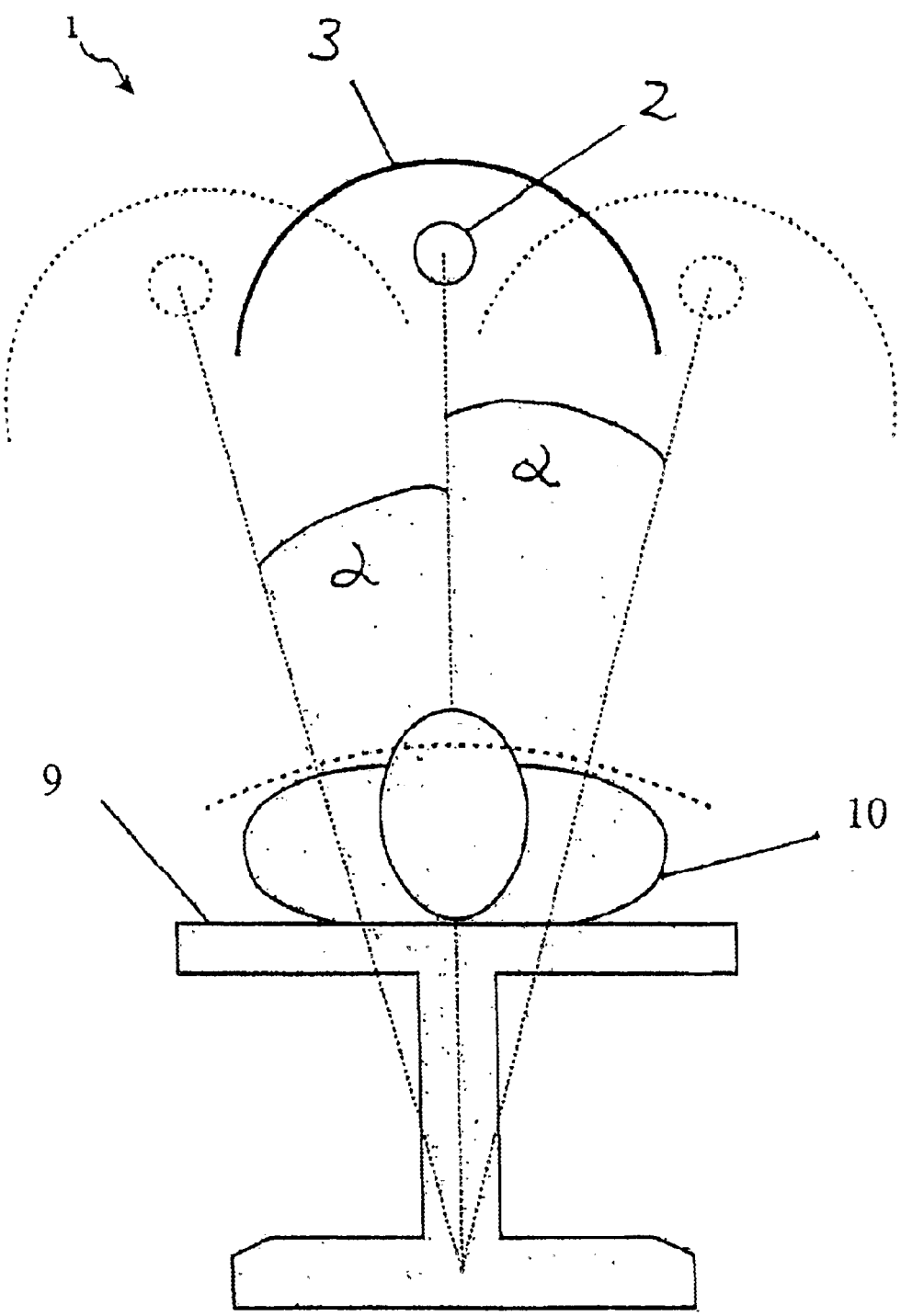
Figure 4:
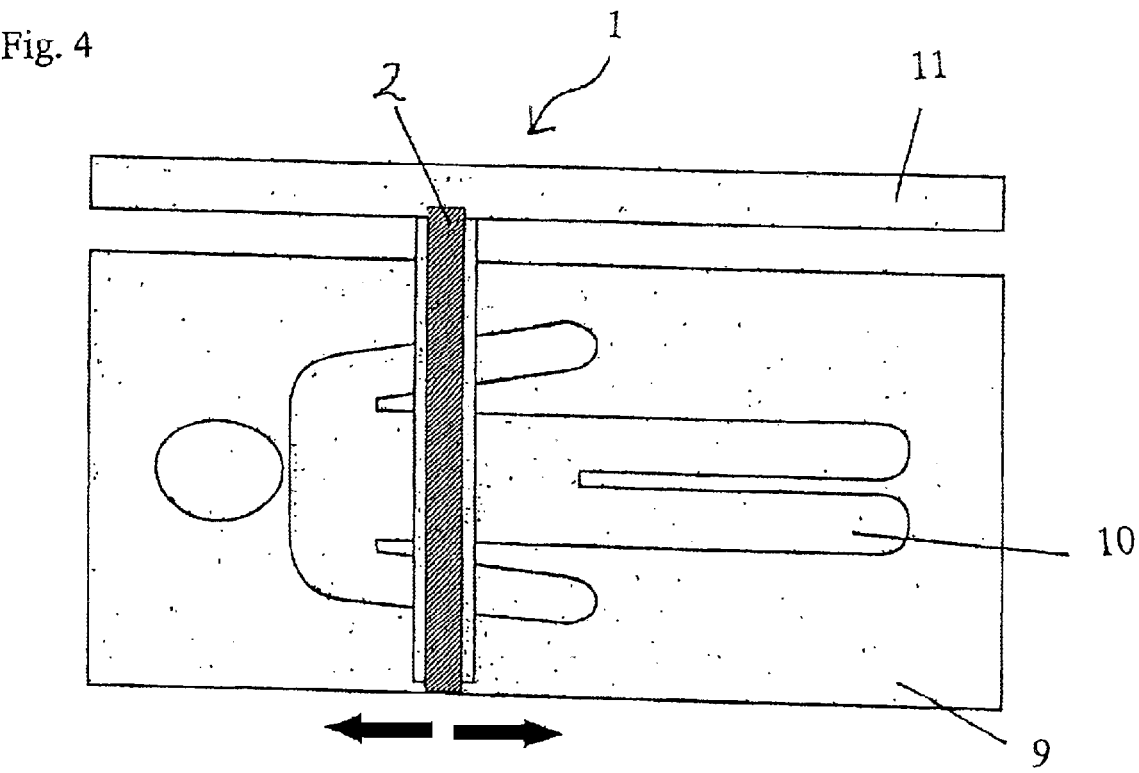
Figure 5:
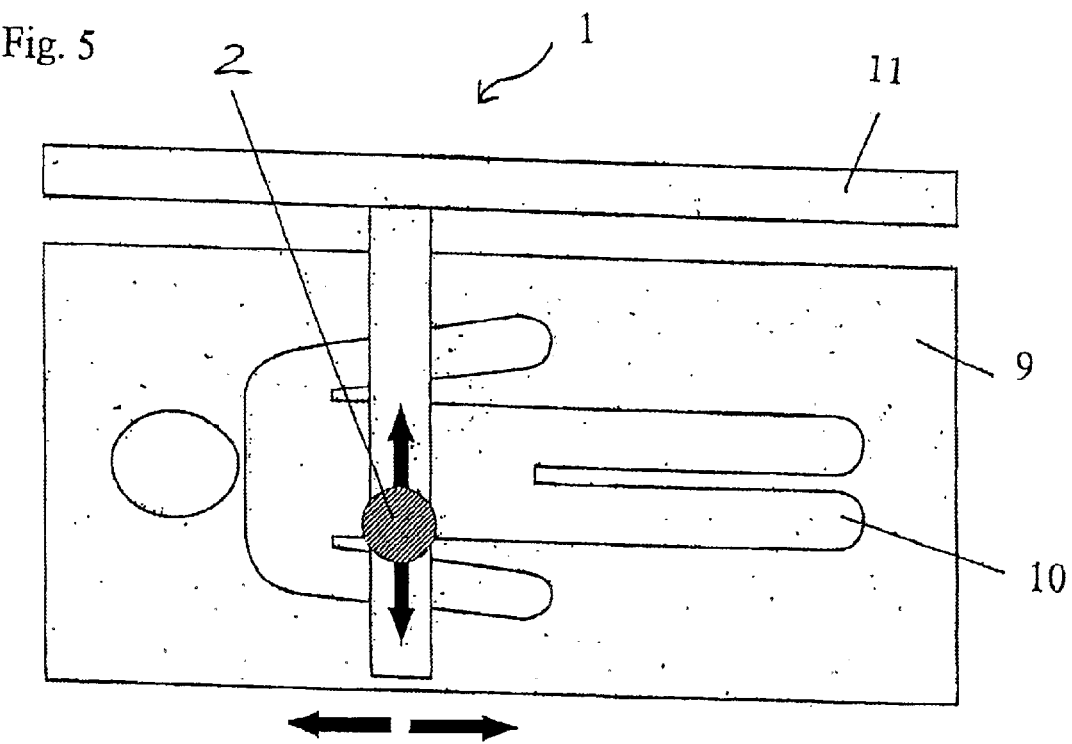
Figure 6A:
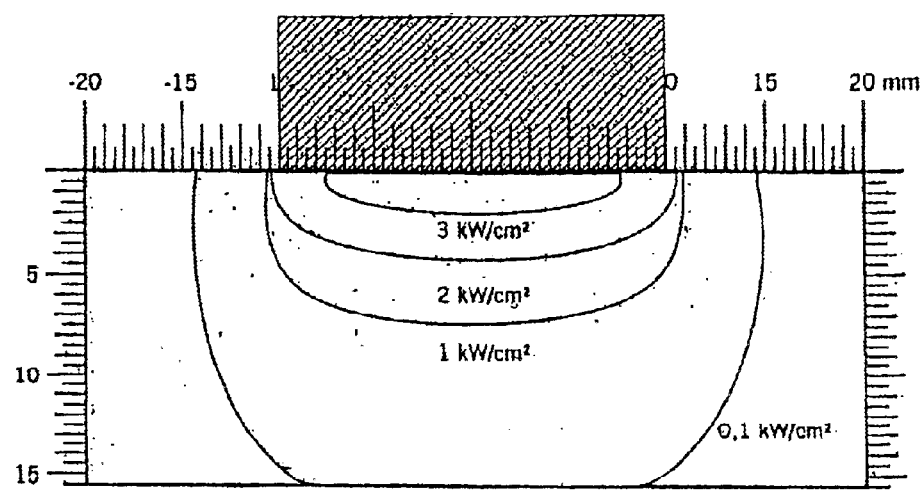
Figure 6B:
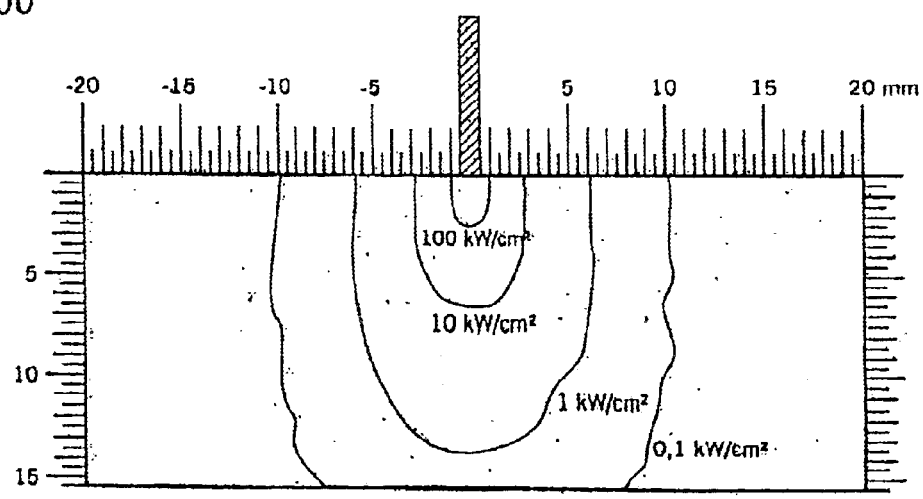
Figure 6C:
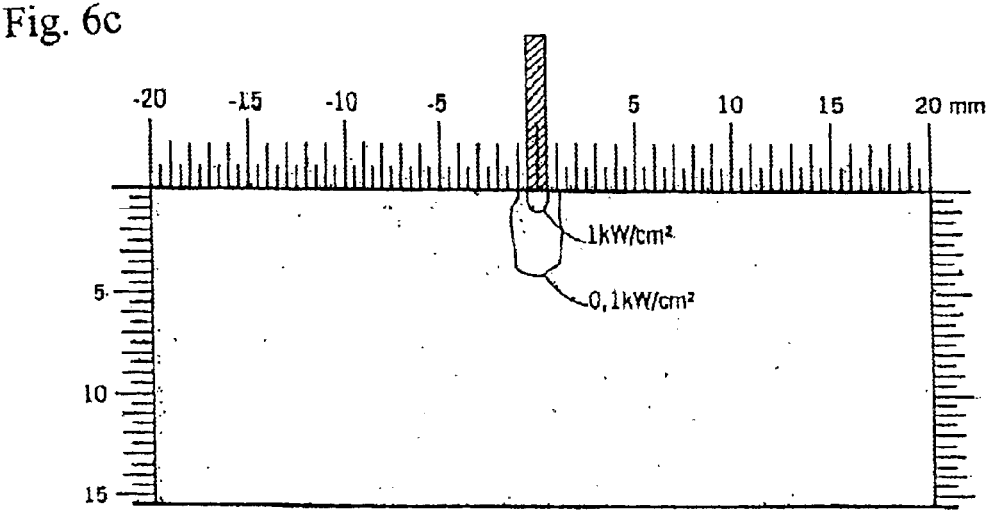
Figure 7:
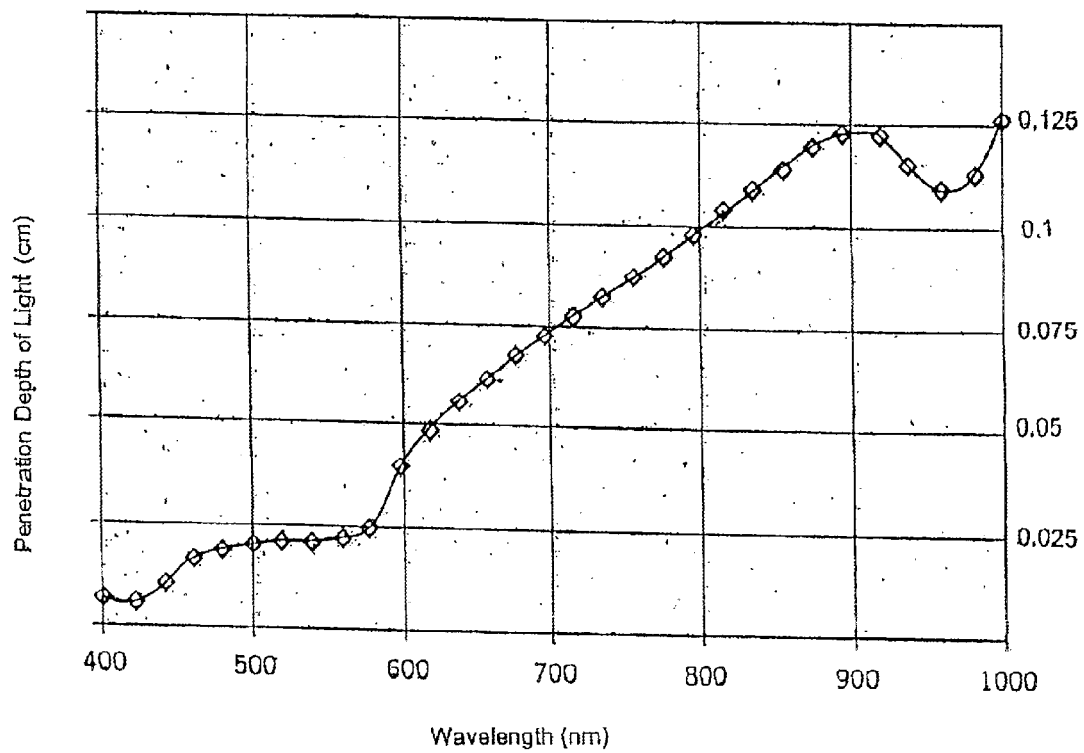
FIG. 7 shows the spectral dependency of the penetration depth (1/e). It is obvious that penetration depth rises steadily between 400 and 900 nm so that it is advisable to increase the green and the red part of the spectrum compared to the blue part, even so if the absorption of the porphyrin decreases compared to the blue part.
Figure 8A:
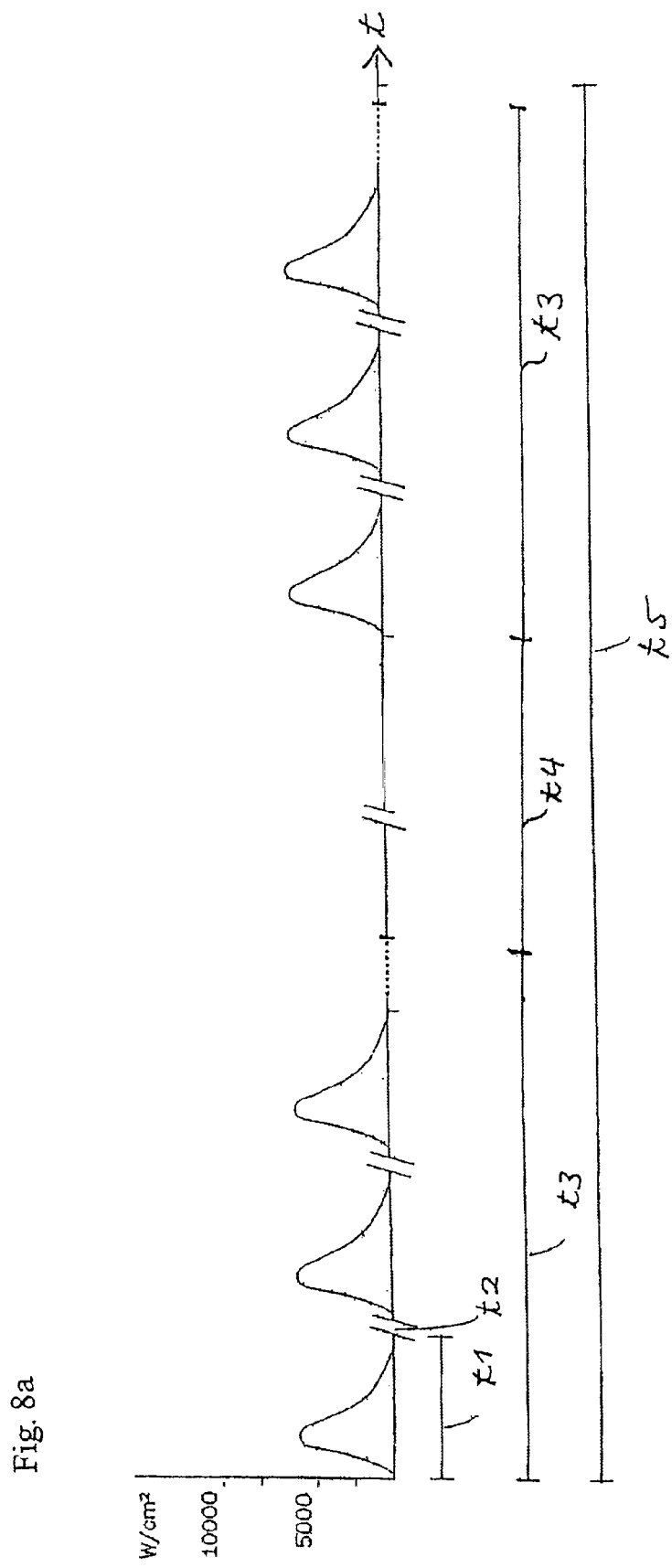
FIG. 8 shows a preferred embodiment of the radiation therapy with a pulsed radiation device and a pulse peak of 5 kW/cm². A train of pulses resp. flashes is emitted.
Figure 8B:
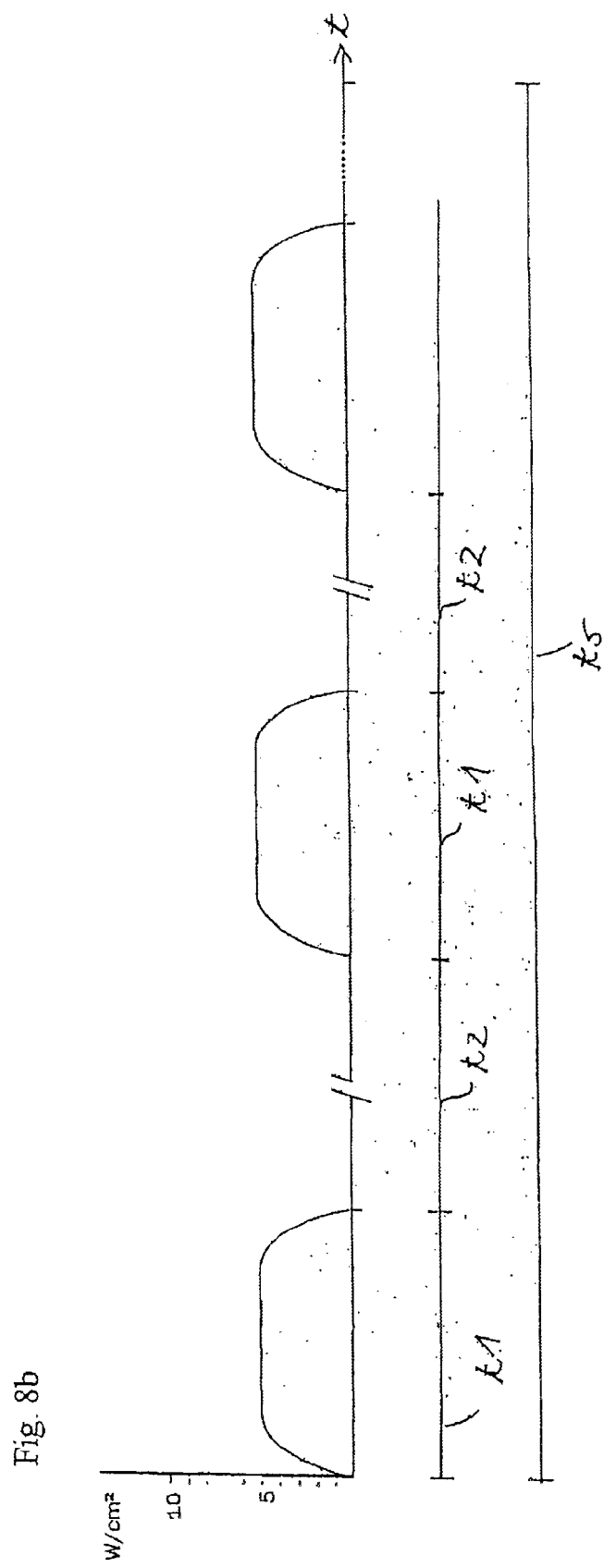

FIG. 8b shows the treatment cycle with an irradiation device according to FIG. 4, the irradiation device being cw-operated. The irradiation peak is at 5 W/cm$^2$, which is considerably lower than that during pulse operation according to FIG. 8a. The period t1 corresponds with the period in which the irradiation device can irradiate a certain area during the scan procedure and lies preferably between 0.1 and 0.5 s. The period t2 is a complete scan period minus the period t1. During this time, oxygen can reperfuse the tissue and the tissue can cool off. t2 is a period between 1 and 300 seconds, preferably between 2–20 seconds.

Figure 8C:
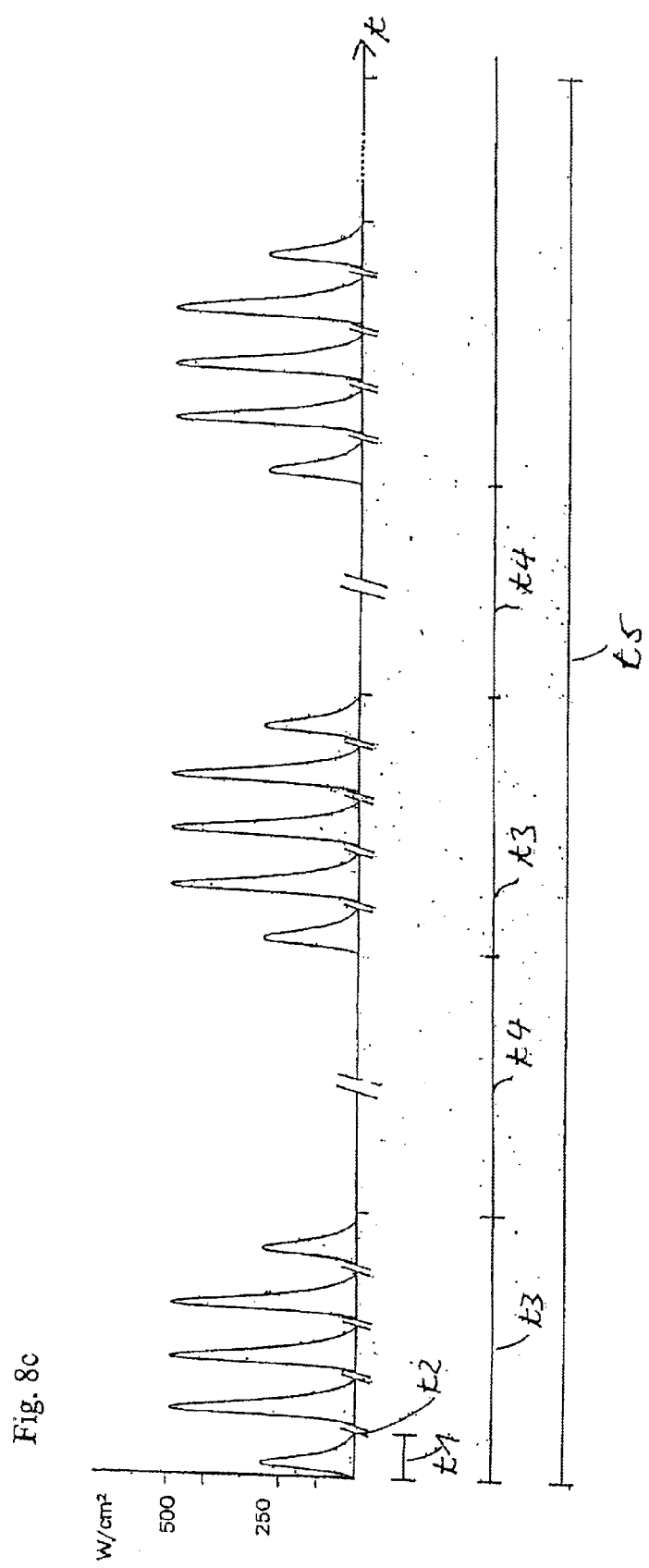

Finally, in FIG. 8c the combination of a scan movement with pulse operation is shown, the irradiation peaks being between 250 and 500 W/cm$^2$. During the period t3, while the irradiation source covers a certain area, preferably 5 pulses are generated, the first and the last pulse only partially reaching the treatment area due to the movement. The preferred effective pulse length is 100 µs and the irradiation source is timed with a frequency of 25 Hz, so that t2 has a duration of 40 ms with an irradiation time t3 of 0.2 s. However, different combinations are possible according to the examples in FIGS. 8a and 8b.

It has been commonly observed that the addition of anti-inflammatory drugs such as cortisone is rather counter-productive. Therefore patients should refrain from taking similar drugs prior to the treatment. The intake of anti-inflammatory substances should be discontinued a few days prior to treatment because of their long-lasting effects. Moreover, it was observed that through a treatment of small areas also caused a healing of non-treated areas of the body. This indicates a locally induced systemic effect of the irradiation which appears to work similar to an immunization and/or desensibilization.

Figure 9:
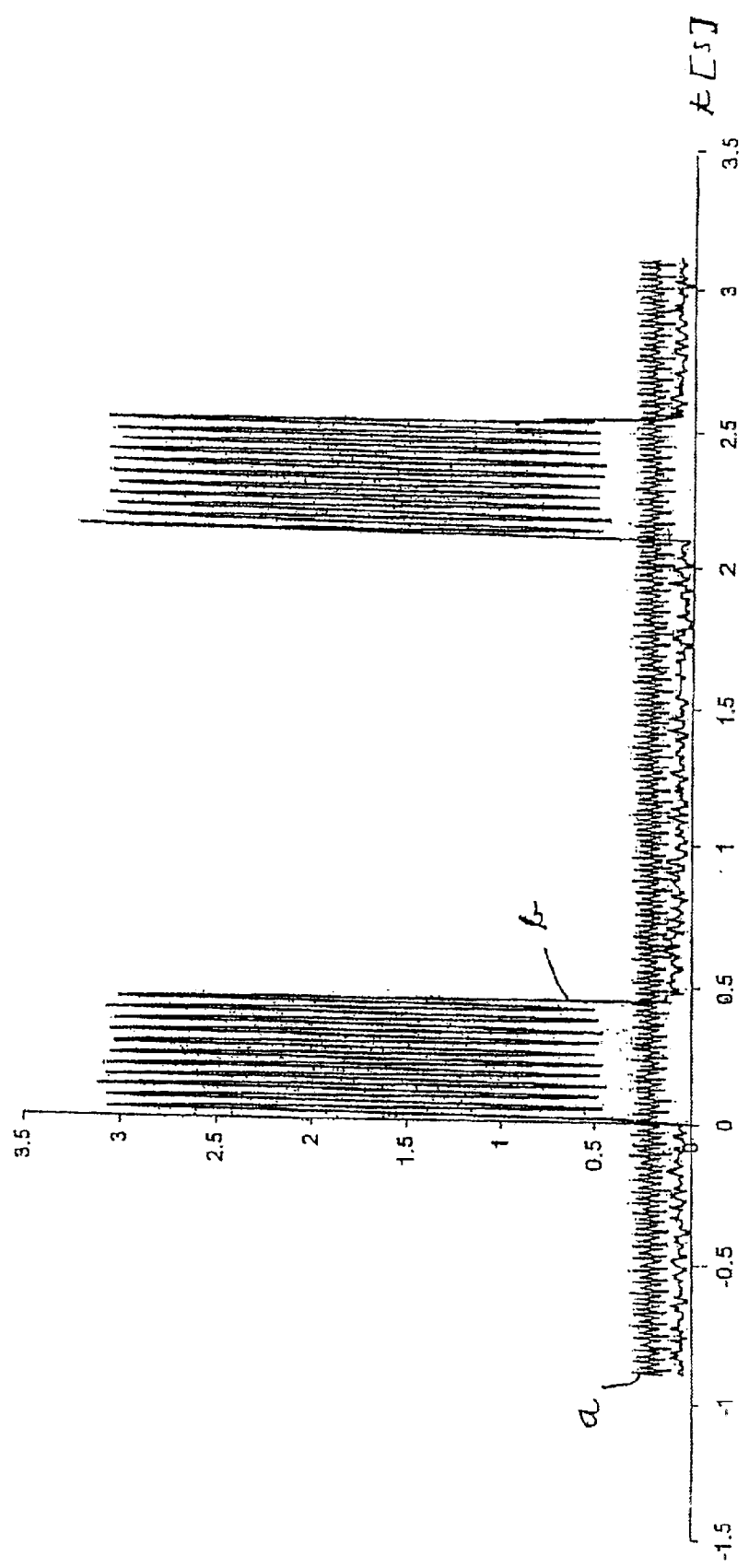
Figure 10:
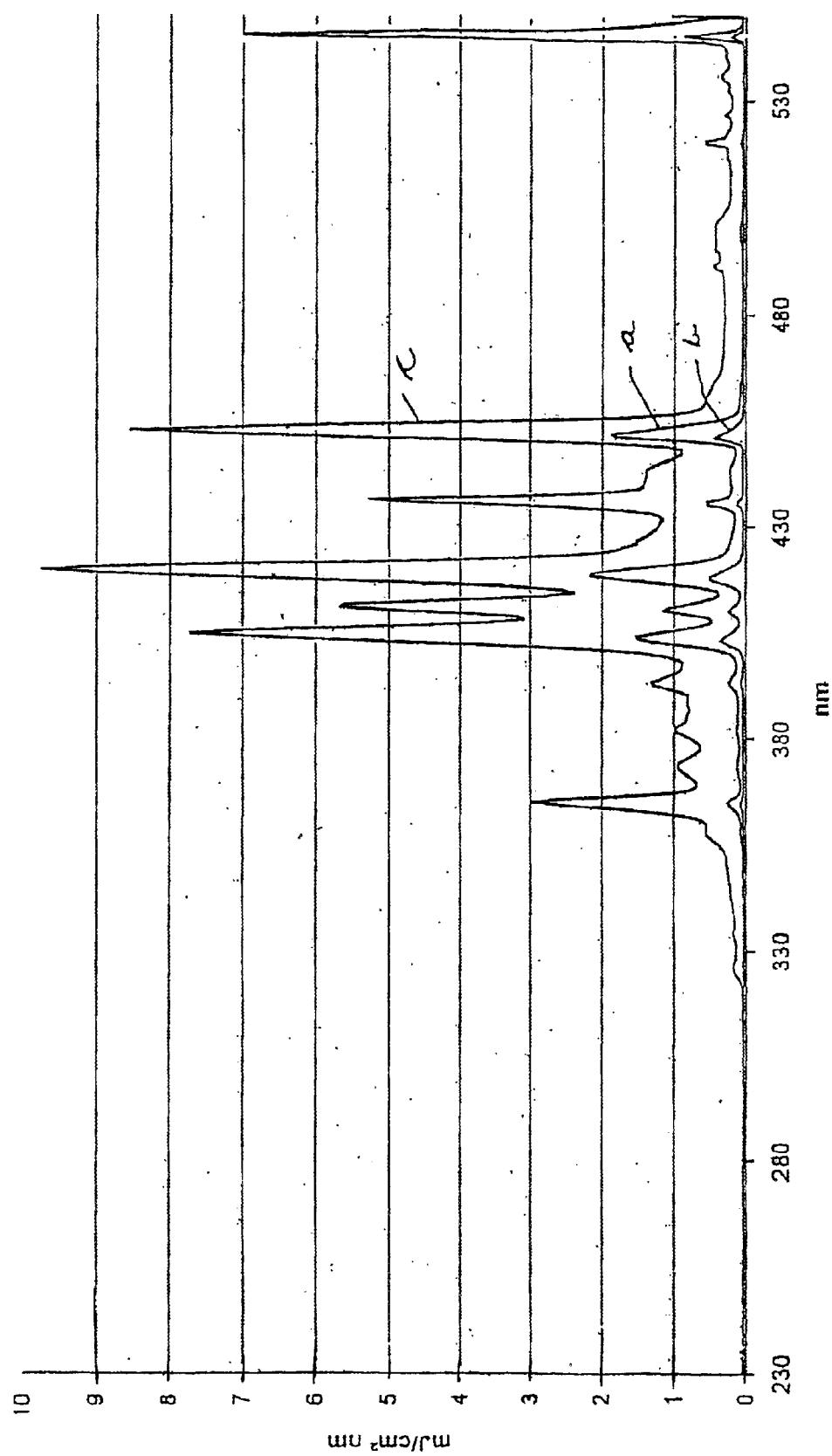

FIG. 9 displays a comparison of the relative irradiation power of a 1000 W gallium iodide-doped mercury lamp in continuous mode operated at 1000 W (curve a) and in pulsed overload operation (curve b). The average power in pulse operation mode is 1500 W. It is obvious that even a small overload induces a marked rise of the optical emission FIG. 10 shows the spectral energy density of a gallium iodide-doped mercury lamp with a normal operating power of 1000 W if the input power is changed. Curve a represents the spectral energy density under cw-operating conditions at 1000 W. Curve b shows the spectral energy density at a lowered load of 100 W, and curve c displays the spectral energy density with an input power of 10 kW. Low load and overload operation were performed in cw-mode. It can be seen that in both cases the spectral lines of the gallium emission remain stable and there is no inversion of spectral lines. Furthermore, there is an enormous proportional increase of the emission.

Figure 11:
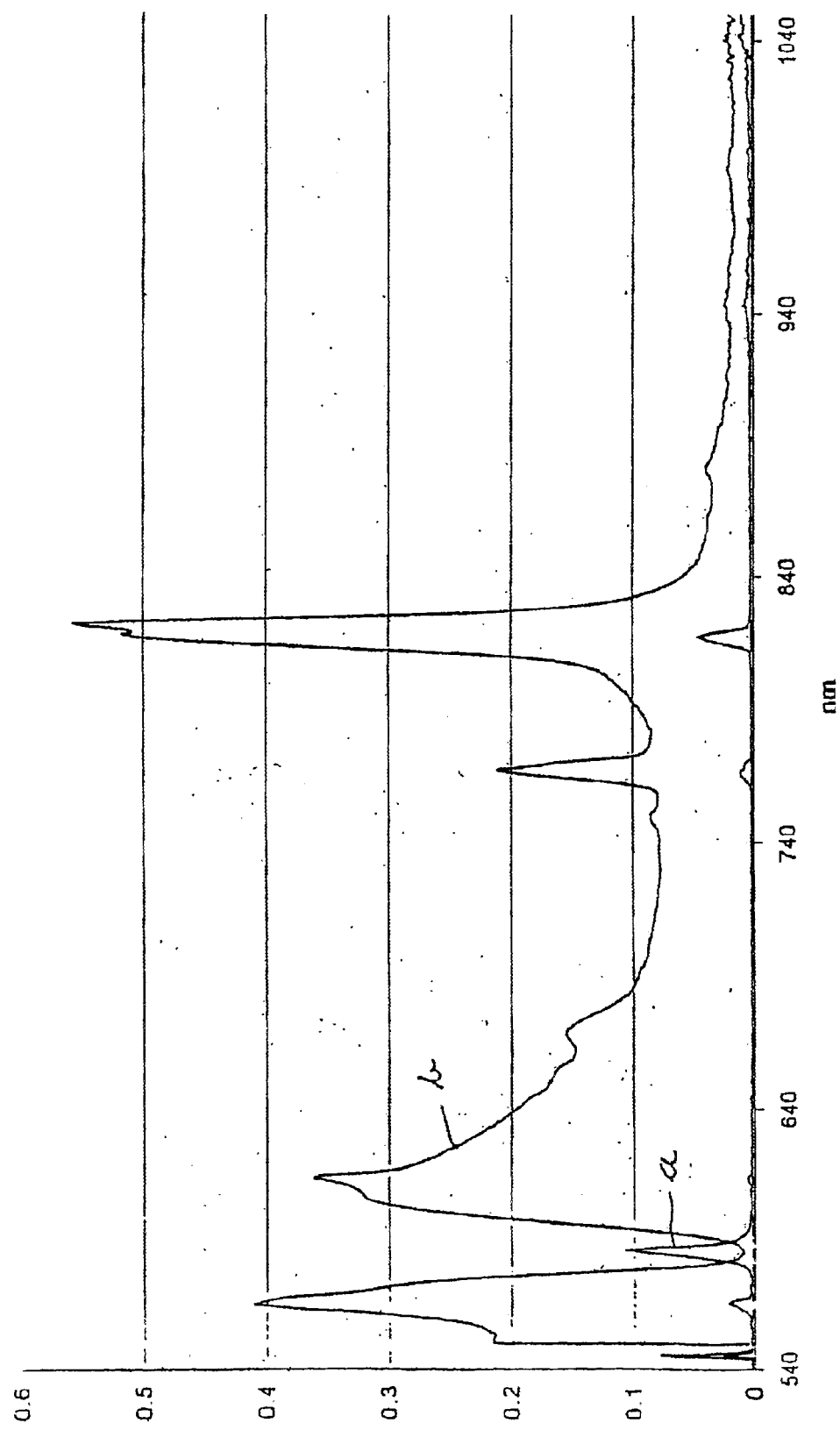

In contrast, FIG. 11 shows the different behavior of a sodium vapor lamp. Curve b shows that pulsed operation with 700 W using a lamp with normal operation power of 230 W induces a complete inversion of the sodium spectral emission around 488 nm. For comparison, curve a shows the relative irradiance at cw-operation under normal power conditions.

Figure 12:
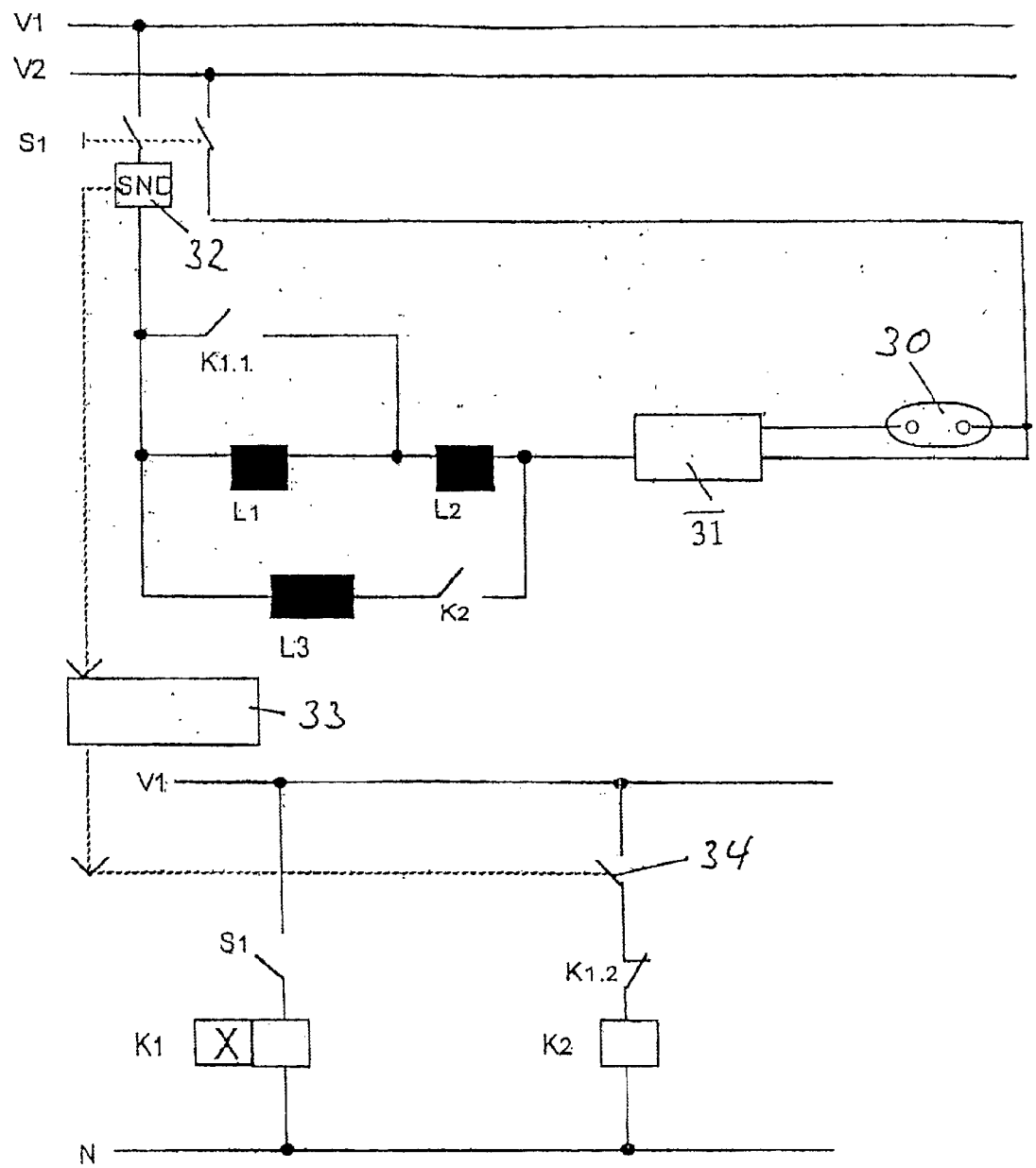

FIG. 12 shows a circuit arrangement for the pulsed overload operation of a gallium iodide-doped mercury lamp. The circuit includes a gallium iodide-doped mercury lamp 30, an ignition device 31, a zero current detector 32, a pulse generator 33, a first relay K1 and a second relay K2, a starter switch S1 and a pulse switch 34. Both relays K1 and K2 are connected to a neutral conductor N and the first phase of a three-phase circuit. The gallium iodide-doped mercury lamp 30 is connected to the second phase V2 of the three-phase-circuit via an auxiliary contact. Via a second auxiliary contact of the starter switch S1 the first phase V1 is connected to the ignition device 31 via the zero current detector 32 via a coil arrangement. The coils L1 and L2 are connected in serially. A third coil L3 is connected in parallel to the aforementioned serial coils and is switched with the contact K2 which belongs to the second relay K2. in parallel to the first coil L1 there is another contact K1.1 which relates to the first relay K1. A second contact K1.2 which belongs to the first relay K1 is switched between the second relay K2 and the pulse switch 34. The principal function of this circuit arrangement is described as follows: By closing the starter switch S1, the related auxiliary contacts also close. Therefore, the contact K1 closes and the contact K 1.2 opens resp. stays open. The first phase V1 of the three phase circuit is connected via the closed contact K1.1 through coil L2 with the ignition device 31. In this arrangement coil L2 functions as an inductive coil limiting the lamp current. This switching condition remains until the gallium iodide-doped mercury lamp 30 has reached normal operational conditions. Then the relay K1 opens which may be a tripping relay of a windshield wiper. The opening of relay K1 induces the opening of the contact K1.1 and the simultaneous closing of contact K1.2. This activates relay K2 and the coil L1 is switched in series to coil L2. In this arrangement, coil L2 acts as a simmer coil. Since the pulse switch 34 is still open, the contact K2 also remains open. In this condition, the gallium iodide-doped mercury lamp 30 operates in a simmer mode. Pulsed operation is started by the pulse generator 33, if the zero current detector 32 detects zero current at the first phase V1 of the three-phase circuit. Now the pulse switch 34 switches and through activation of relay K2, the contact K2 is closed. Now the coil L3 is switched in a parallel manner, which lowers the total inductivity of the arrangement. Through this, the ignition device 31 receives an overload pulse. At the end of the pulse the pulse generator 33 opens the pulse switch 34. This closes contact K2 and the gallium iodide-doped mercury lamp 30 operates again through the serial arrangement of coils L1 and L2 as long as the next pulse is being generated by the pulse generator 33.

Figure 13:
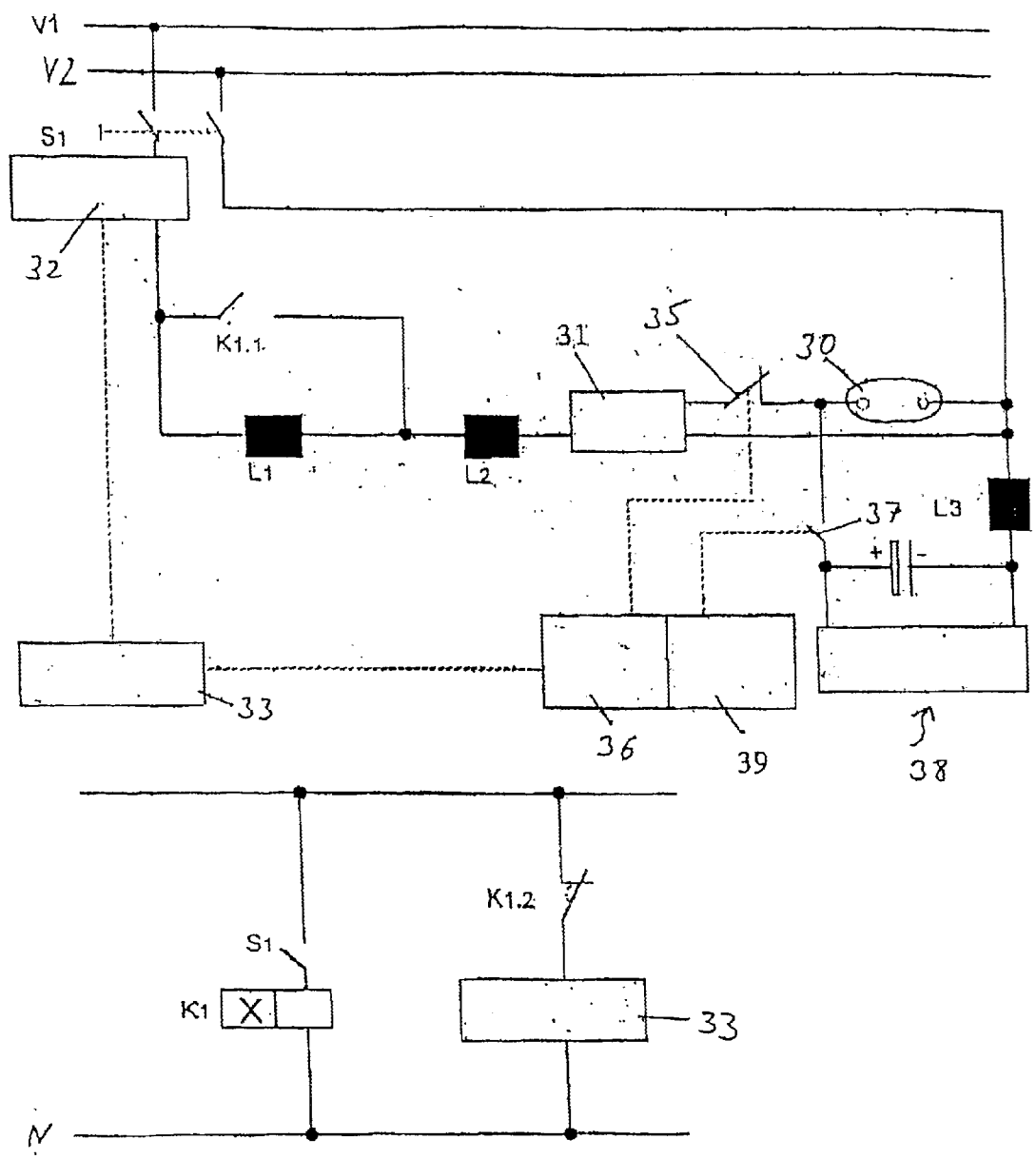

FIG. 13 shows an alternative embodiment with a capacitor bank. All elements which relate to FIG. 9 have been given the same numbers. In contrast to the embodiment in FIG. 9 a TRIAC 35 is arranged between the ignition device 31 and the gallium iodide-doped mercury lamp 30. The TRIAC driver 36 is triggered by the pulse generator 32.

The capacitor bank 38 is connected to the electrodes of the gallium iodide-doped mercury lamp 30 via an IGBT 37 resp. the coil L3. The driver 39 of the IGBT 37 is also triggered by the pulse generator 33. The functioning of the device is as follows: Again, the starter switch S1 is closed, which also closes K1.1 and opens the contact K1.2. The activated TRIAC 35 allows the operation of the gallium iodide-doped mercury lamp 30 under normal load. After that, the relay K1 opens, the contact K1.1 opens and K1.2 closes. The gallium iodide-doped mercury lamp 30 is being operated in a simmer mode via the serial arrangement of coils L1 and L2 while the pulse generator 33 is activated. In order to allow pulse operation, the zero current detector 32 detects zero current and transmits this information to the pulse generator 33. This generator activates the drivers 33 and 39 in a way that the TRIAC 35 blocks and the IGBT 37 contacts. This switches the capacitor bank to the gallium iodide-doped mercury lamp 30 and disconnects the lamp from the supply voltage. At the end of a pulse, the IGBT 37 blocks and TRIAC 35 conducts in a way that the gallium iodide-doped mercury lamp 30 is operating in simmer mode again via coils L1 and L2. It is understood that the coils in the aforementioned technical example relate to general inductivities which could be realized differently. For demonstration of the magnitudes the following examples for the coils L1, L2 and L3 are given. L1=500 mH; L2=150 mH and L3=7 mH.

Pulse operation: 1eff=40 A resp. 11.8 A/cm$^2$, 1 peak=55 A resp. 16.2 A/cm$^2$

Simmer mode: 1eff=1.2 A resp. 0.35 A/cm$^2$, 1 peak=1.7 A resp. 0.5 A/cm$^2$

Normal operation 1eff=5 A resp. 1.5 A/cm$^2$, 1 peak=7 A resp. 2 A/cm$^2$

What is claimed is:

1. An irradiation device for the treatment of totally or partially cell mediated inflammations of the skin and the viscera, comprising at least one UV emitting radiation source for the irradiation of larger areas to be treated, the emitted wavelength on the treatment area being at least 400 nm and comprising a wavelength range of 400–500 nm, wherein less than 7% of the overall optical output are emitted in the UV range, and wherein at least 30% of the optical output are emitted in the range of 400–500 nm; and a phosphor material with UVC-transparent carrier material arranged in front of the radiation source, wherein said UVC-transparent carrier material is a fluorescent foil made of silicone elastomer or fluoropolymer doped with anorganic phosphor particles, wherein the irradiation device comprises means for the generation of optical pulses on the area to be treated, the generated optical pulses having a peak irradiation intensity and an energy density, the peak irradiation intensity of the generated optical pulses being higher than 0.5 W/cm$^2$ and lower than 100 kW/cm$^2$, the energy density of one emitted optical pulse being between 0.05 and 10 J/cm$^2$.

2. Irradiation device according to claim 1, wherein the energy density of one emitted optical pulse is between 0.3–0.8 J/cm$^2$.

3. Irradiation device according to claim 1, wherein the generated optical pulses have a cw-irradiation intensity, where the average cw-irradiation intensity of one optical pulse is between 1 mW/cm$^2$–10 W/cm$^2$.

4. Irradiation device according to claim 1, wherein the radiation source is controlled by being one or the other or both (i) movable in relation to the area to be irradiated and (ii) pulse operable to control the length of a pulse.

5. Irradiation device according to claim 4, wherein the pulse length is between 1 µs–500 ms.

6. Irradiation device according to claim 5, wherein said radiation source has a pulse frequency of 0.01–100 Hz.

7. Irradiation device according to claim 1, wherein said radiation source is a xenon- or deuterium flashlamp or an overload-pulse operated gallium iodide-doped mercury lamp with a device for the cutting off and/or transformation of the UV parts and other undesired parts of the spectrum within the desired area of the spectrum.

8. Irradiation device according to claim 1, wherein said carrier material or the luminescent foil is doped with at least one of: (i) the following phosphors fluorescent in the spectral range of 410–490 nm: $Sr_2P_2O_7$:Eu, $Sr_5(PO_4)_3Cl$:Eu, $BaMg_2Al_{16}O_{27}$:Eu, $CaWO_4$: Pb; $(Sr,Ca,Ba)_5(PO_4)_3Cl$:Eu;$Sr_2P_2O_7$:Sn,$(Ba,Ca)_5(PO_4)_3Cl$:Eu) (ii) the following phosphors fluorescent in the spectral range of 510–560 nm: $ZnSiO_4$:Mn;$MgAl_{11}O_{19}$:Ce,Tb, Mn;$YBO_3$:Tb;$LaPO_4$:Ce,Tb; or (iii) the following phosphors fluorescent in the spectral range of 610–670 nm: $Y_2O_3$:Eu;$Y(P,V)O_4$:Eu; $CaSiO_3$:Pb,Mn; $(Sr,Mg)_3(PO_4)_2$:Sn; $3.5MgO*0.5MgF_2*GeO_2$:Mn.

9. Irradiation device according to claim 1, wherein the radiation source has means for operating said radiation source in simmer mode.

10. Irradiation device according to claim 1, wherein said radiation source is equipped with cooling means for cooling one or the other or both of the area to be irradiated and the fluorescent foil.

11. Irradiation device according to claim 10, wherein said cooling means is designed as an air cooling means.

12. Irradiation device according to claim 1, wherein said irradiation device has associated means for the topical or inhalative admission of oxygen.

13. Irradiation device according to claim 1, wherein the irradiation source has additional emission in the range of one or the other or both of (i) 520–550 nm and (ii) 610–670 nm.

14. Irradiation device according to claim 1, wherein said radiation source is enclosed by a paraboloid or ellipsoid reflector.

15. Irradiation device according to claim 1, wherein the at least one UV emitting radiation source emits a beam of radiation having a beam diameter, and wherein the beam diameter of the emitted radiation is at least in one dimension wider than 10 mm and narrower than 100 mm.

16. Irradiation device according to claim 1,
wherein the energy density of one emitted optical pulse is between 0.3–0.8 J/cm$^2$,
wherein the copy underlined text from claim 21 to here average cw-irradiation intensity of one optical pulse is between 1 mW/cm$^2$–10 W/cm$^2$,
wherein the radiation source is pulse operable and/or movable in relation to the area to be irradiated,
wherein the effective pulse length is between 1 µs–500 ms,
wherein said radiation source has a pulse frequency of 0.01–100 Hz,
wherein said radiation source is a xenon- or deuterium flashlamp or an overload-pulse operated gallium iodide-doped mercury lamp with a device for the cutting off and/or transformation of the UV parts and other undesired parts of the spectrum within the desired area of the spectrum,
a phosphor material with UVC-transparent carrier material being arranged in front of the radiation source, wherein the transparent carrier material is a fluorescent foil made of silicone elastomer or fluorpolymer doped with anorganic phosphor particles, wherein said carrier material or the luminescent foil is doped with at least one of: (i) the following phosphors fluorescent in the spectral range of 410–490 nm: $Sr_2P_2O_7:Eu$, $Sr_5(PO_4)_3Cl:Eu$, $BaMg_2Al_{16}O_{27}:Eu$, $CaWO_4:Pb;(Sr,Ca,Ba)_5(PO_4)_3Cl:Eu;Sr_2P_2O_7:Sn,(Ba,Ca)_5(PO_4)_3Cl:Eu)$; (ii) the following phosphors fluorescent in the spectral range of 510–560 nm $ZnSiO_4:Mn;MgAl_{11}O_{19}:Ce,Tb,Mn;YBO_3:Tb;LaPO_4:Ce,Tb$ (iii) the following phosphors fluorescent in the spectral range of 610–670 nm $Y_2O_3:Eu;Y(P,V)O_4:Eu$; $CaSiO_3:Pb,Mn$; $(Sr,Mg)_3(PO_4)_2:Sn$; $3.5MgO*0.5MgF_2*GeO_2:Mn$, wherein the pulsed radiation source has means for operating said radiation source in simmer mode, wherein said radiation source is equipped with cooling means for cooling one or the other or both of the area to be irradiated and the fluorescent foil, wherein said cooling means is designed as an air cooling means, wherein said irradiation device has associated means for the topical or inhalative admission of oxygen, wherein the irradiation source has additional emission in the range of one or the other or both of (i) 520–550 nm and (ii) 610–670 nm, wherein said radiation source is enclosed by a paraboloid or ellipsoid reflector, and wherein the at least one UV emitting radiation source emits a beam of radiation having a beam diameter, and wherein the beam diameter of the emitted radiation is at least in one dimension wider than 10 mm and narrower than 100 mm.

17. Method particularly for the treatment of totally or partially cell mediated inflammations of the skin, connective tissue and the viscera, in particular atopic dermatitis cutaneous T-cell lymphoma, lichen rubber, alopecia areata, systemic lupus erythematodes, psoriasis and scleroderma, including other connective tissue diseases, multiple sclerosis, uveitis, Morbus Crohn and other diseases with an immunological background, including the treatment of infectious diseases such as herpes, papilloma virus, fungus, HIV, prions and burn wounds and disturbed wound healing through bacterial infection comprising the steps of, providing at least one radiation source for the irradiation of the treatment area, the emitted wavelength on the treatment area being at least 400 nm and comprising a wavelength range of 400–500 nm, and a phosphor material with UVC-transparent carrier material arranged in front of the radiation source, wherein said UVC-transparent carrier material is a fluorescent foil made of silicone elastomer or fluoropolymer doped with anorganic phosphor particles, generating optical pulses of radiation from the radiation source, the generated optical pulses having a peak irradiation intensity and an energy density, the peak irradiation intensity of the generated optical pulses being higher than 0.5 $W/cm^2$ and lower than 100 $kW/cm^2$, the energy density of one emitted optical pulse being between 0.05 and 10 $J/cm^2$, and applying the optical pulses to the treatment area.

18. Method according to claim 17 wherein the energy density of one emitted optical pulse is between 0.3–0.8 $J/cm^2$.

19. Method according to claim 17, wherein the generated optical pulses have a cw-irradiation intensity, where the average cw-irradiation intensity of one optical pulse is between 1 $mW/cm^2$–10 $W/cm^2$.

20. An irradiation device for the treatment of totally or partially cell mediated inflammations of the skin and the viscera, comprising at least one radiation source for the irradiation of larger areas to be treated, the emitted wavelength on the treatment area being at least 400 nm and comprising a wavelength range of 400–500 nm;

wherein the irradiation device comprises means for the generation of optical pulses on the area to be treated, the generated optical pulses having a peak irradiation intensity and an energy density, the peak irradiation intensity of the generated optical pulses being higher than 0.5 $W/cm_2$ and lower than 100 $kW/cm_2$, the energy density of one emitted optical pulse being between 0.05 and 10 $J/cm^2$; and wherein the radiation source has means for operating said radiation source in simmer mode.

21. An irradiation device for the treatment of totally or partially cell mediated inflammations of the skin and the viscera, comprising at least one radiation source for the irradiation of larger areas to be treated, the emitted wavelength on the treatment area being at least 400 nm and comprising a wavelength range of 400–500 nm, and a phosphor material with UVC-transparent carrier material arranged in front of the radiation source, wherein said UVC-transparent carrier material is a fluorescent foil made of silicone elastomer or fluoropolymer doped with anorganic phosphor particles, wherein the irradiation device comprises means for the generation of optical pulses on the area to be treated, the generated optical pulses having a peak irradiation intensity and an energy density, the peak irradiation intensity of the generated optical pulses being higher than 0.5 $W/cm^2$ and lower than 100 $kW/cm^2$, the energy density of one emitted optical pulse being between 0.05 and 10 $J/cm^2$;

wherein said radiation source is equipped with cooling means for cooling one or the other or both of the area to be irradiated and the fluorescent foil.

22. Irradiation device according to claim 21, wherein said cooling means is designed as an air cooling means.

23. An irradiation device for the treatment of totally or partially cell mediated inflammations of the skin and the viscera, comprising at least one radiation source for the irradiation of larger areas to be treated, the emitted wavelength on the treatment area being at least 400 nm and comprising a wavelength range of 400–500 nm, wherein the irradiation device comprises means for the generation of optical pulses on the area to be treated, the generated optical pulses having a peak irradiation intensity and an energy density, the peak irradiation intensity of the generated optical pulses being higher than 0.5 $W/cm^2$ and lower than 100 $kW/cm^2$, the energy density of one emitted optical pulse being between 0.05 and 10 $J/cm^2$;

wherein said irradiation device has associated means for the topical or inhalative admission of oxygen.

24. The irradiation device of claim 23, comprising a phosphor material with UVC-transparent carrier material arranged in front of the radiation source, wherein said carrier is doped with at least one phosphor fluorescent in the spectral range of 410–490 nm.

25. The irradiation device of claim 24, wherein the at least one phosphor comprises at least one of the following phosphors:

$Sr_2P_2O_7$:Eu,$Sr_5(PO_4)_3$Cl:Eu,$BaMg_2Al_{16}O_{27}$:Eu, $CaWO_4$:Pb;$(Sr,Ca,Ba)_5(PO_4)_3$Cl:Euu,;$Sr_2P_2O_7$:Sn, $(Ba,Ca)_5(PO_4)_3$Cl:Eu.

26. An irradiation device for the treatment of totally or partially cell mediated inflammations of the skin and the viscera, comprising at least one UV emitting radiation source for the irradiation of larger areas to be treated, the emitted wavelength on the treatment area being at least 400 nm and comprising a wavelength range of 400–500 nm, wherein less than 7% of the overall optical output are emitted in the UV range, and wherein at least 30% of the optical output are emitted in the range of 400–500 nm;

wherein the irradiation device comprises means for the generation of optical pulses on the area to be treated, the generated optical pulses having a peak irradiation intensity and an energy density, the peak irradiation intensity of the generated optical pulses being higher than 0.5 W/cm$^2$ and lower than 100 kW/cm$^2$, the energy density of one emitted optical pulse being between 0.05 and 10 J/cm$^2$;

wherein the energy density of one emitted optical pulse is between 0.3–0.8 J/cm$^2$, wherein the copy underlined text from claim 21 to here average cw-irradiation intensity of one optical pulse is between 1 mW/cm$^2$–10 W/cm$^2$, wherein the radiation source is pulse operable and/or movable in relation to the area to be irradiated, wherein the effective pulse length is between 1 $\mu$s–500 ms, wherein said radiation source has a pulse frequency of 0.01–100 Hz, wherein said radiation source is a xenon- or deuterium flashlamp or an overload-pulse operated gallium iodide-doped mercury lamp with a device for the cutting off and/or transformation of the UV parts and other undesired parts of the spectrum within the desired area of the spectrum, a phosphor material with UVC-transparent carrier material being arranged in front of the radiation source, wherein the transparent carrier material is a fluorescent foil made of silicone elastomer or fluorpolymer doped with anorganic phosphor particles, wherein said carrier material or the luminescent foil is doped with at least one of: (i) the following phosphors fluorescent in the spectral range of 410–490 nm: $Sr_2P_2O_7$:Eu, $Sr_5(PO_4)_3$Cl:Eu, $BaMg_2Al_{16}O_{27}$:Eu, $CaWO_4$:Pb;$(Sr,Ca,Ba)_5(PO_4)_3$Cl:Eu;$Sr_2P_2O_7$:Sn,$(Ba,Ca)_5(PO_4)_3$Cl:Eu); (ii) the following phosphors fluorescent in the spectral range of 510–560 nm $ZnSiO_4$:Mn; $MgAl_{11}O_{19}$:Ce,Tb, Mn;$YBO_3$:Tb;$LaPO_4$:Ce,Tb; (iii) the following phosphors fluorescent in the spectral range of 610–670 nm: $Y_2O_3$:Eu;$Y(P,V)O_4$:Eu; $CaSiO_3$:Pb,Mn; $(Sr,Mg)_3(PO_4)_2$:Sn; $3.5MgO*0.5MgF_2*GeO_2$:Mn;

wherein the pulsed radiation source has means for operating said radiation source in simmer mode, wherein said radiation source is equipped with cooling means for cooling one or the other or both of the area to be irradiated and the fluorescent foil, wherein said cooling means is designed as an air cooling means, wherein said irradiation device has associated means for the topical or inhalative admission of oxygen, wherein the irradiation source has additional emission in the range of one or the other or both of (i) 520–550 nm and (ii) 610–670 nm, wherein said radiation source is enclosed by a paraboloid or ellipsoid reflector, wherein the at least one UV emitting radiation source emits a beam of radiation having a beam diameter, and wherein the beam diameter of the emitted radiation is at least in one dimension wider than 10 mm and narrower than 100 mm.

\* \* \* \* \*

UNITED STATES PATENT AND TRADEMARK OFFICE
CERTIFICATE OF CORRECTION

| | | |
|---|---|---|
| PATENT NO. | : 6,902,563 B2 | Page 1 of 1 |
| APPLICATION NO. | : 10/094430 | |
| DATED | : June 7, 2005 | |
| INVENTOR(S) | : Jan Hennrik Wilkens and Rolf Stirner | |

It is certified that error appears in the above-identified patent and that said Letters Patent is hereby corrected as shown below:

Column 16, Claim 16, line 51, delete "copy underlined text from claim 21 to here" and replace with --generated optical pulses have a cw-irradiation intensity, where the--

Column 19, Claim 26, line 23, delete "copy underlined text from claim 21 to here" and replace with --generated optical pulses have a cw-irradiation intensity, where the--

Column 19, Claim 25, line 2, "$CaWO_4:Pb;(Sr,Ca,Ba)_5(PO_4)3Cl:Euu,;Sr_2P_2O_7:Sn$" and replace with --$CaWO_4:Pb;(Sr,Ca,Ba)_5(PO_4)3Cl:Eu,;Sr_2P_2O_7:Sn$--

Signed and Sealed this

Nineteenth Day of August, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,902,563 B2 | Page 1 of 1 |
| APPLICATION NO. | : 10/094430 | |
| DATED | : June 7, 2005 | |
| INVENTOR(S) | : Jan Henrik Wilkens and Rolf Stirner | |

It is certified that error appears in the above-identified patent and that said Letters Patent is hereby corrected as shown below:

On the front page of the Patent, under the "Inventors" section, Jan Hennrik Wilkens should read as Jan Henrik Wilkens.

Signed and Sealed this

Fourteenth Day of April, 2009

JOHN DOLL
*Acting Director of the United States Patent and Trademark Office*